(12) United States Patent
Tykocinski

(10) Patent No.: US 11,332,539 B2
(45) Date of Patent: *May 17, 2022

(54) FUSION PROTEINS THAT FACILITATE CANCER CELL DESTRUCTION

(71) Applicant: THOMAS JEFFERSON UNIVERSITY, Philadelphia, PA (US)

(72) Inventor: Mark L. Tykocinski, Merion Station, PA (US)

(73) Assignee: Thomas Jefferson University, Philadelphia, PA (US)

( * ) Notice: Subject to any disclaimer, the term of this patent is extended or adjusted under 35 U.S.C. 154(b) by 284 days.

This patent is subject to a terminal disclaimer.

(21) Appl. No.: 15/830,923

(22) Filed: Dec. 4, 2017

(65) Prior Publication Data
US 2018/0148512 A1 May 31, 2018

Related U.S. Application Data

(63) Continuation of application No. 14/763,701, filed as application No. PCT/US2014/014189 on Jan. 31, 2014, now Pat. No. 9,873,747.

(60) Provisional application No. 61/759,301, filed on Jan. 31, 2013.

(51) Int. Cl.
| | | |
|---|---|---|
| *C07K 16/28* | (2006.01) | |
| *C07K 14/525* | (2006.01) | |
| *C07K 14/705* | (2006.01) | |
| *C07K 14/78* | (2006.01) | |
| *C07K 14/47* | (2006.01) | |
| *A61K 38/00* | (2006.01) | |

(52) U.S. Cl.
CPC ...... *C07K 16/2896* (2013.01); *C07K 14/4703* (2013.01); *C07K 14/525* (2013.01); *C07K 14/70575* (2013.01); *C07K 14/78* (2013.01); *A61K 38/00* (2013.01); *C07K 2319/00* (2013.01); *C07K 2319/33* (2013.01); *C07K 2319/74* (2013.01)

(58) Field of Classification Search
None
See application file for complete search history.

(56) References Cited

U.S. PATENT DOCUMENTS

| | | | | |
|---|---|---|---|---|
| 9,873,747 | B2 * | 1/2018 | Tykocinski | C07K 14/70575 |
| 2002/0128438 | A1 * | 9/2002 | Seol | C07K 14/70575 |
| | | | | 530/350 |
| 2002/0160416 | A1 * | 10/2002 | Boyle | C07K 14/70575 |
| | | | | 435/7.1 |
| 2009/0226435 | A1 | 9/2009 | Khare et al. | |
| 2010/0048478 | A1 | 2/2010 | Tykocinski et al. | |
| 2010/0239578 | A1 | 9/2010 | Danska et al. | |
| 2010/0239579 | A1 | 9/2010 | Smith et al. | |
| 2011/0014110 | A1 | 1/2011 | Sirkar et al. | |
| 2011/0237498 | A1 | 9/2011 | Raymond et al. | |
| 2012/0189625 | A1 | 7/2012 | Wang et al. | |
| 2012/0282174 | A1 | 11/2012 | Weissman et al. | |
| 2013/0011401 | A1 * | 1/2013 | Huber | A61P 11/00 |
| | | | | 424/136.1 |

FOREIGN PATENT DOCUMENTS

| | | | | |
|---|---|---|---|---|
| WO | WO-2008151088 | A9 * | 3/2010 | ............... A61P 7/04 |
| WO | 2010130053 | A1 | 11/2010 | |
| WO | 2011143624 | A2 | 11/2011 | |

OTHER PUBLICATIONS

The International Search Report and the Written Opinion of the International Searching Authority (dated May 6, 2014).
Bremer, et al., "Simultaneous inhibition of epidermal growth factor receptor (EGFR) signaling and enhanced activation of tumor necrosis factor-related apoptosis-inducing ligand (TRAIL) receptor-mediated apoptosis induction by an scFv:sTRAIL fusion protein with specificity", J Biol Chem. 280(11), 2005, 10025-10033.
Bremer, et al., "Target cell-restricted apoptosis induction of acute leukemic T cells by a recombinant tumor necrosis factor-related apoptosis-inducing ligand fusion protein with specificity for human CD7", Cancer Res. 65(8), 2005, 3380-3388.
Dao, et al., "Enhancement of antitumor properties of TRAIL by targeted delivery to the tumor neovasculature", Mol Dancer Ther. 7(4), 2008, 851-861.
Dixon, "Evaluation of the CASP2 docking section", Proteins. Suppl 1,1997, 198-204.
Hatherley, et al., "The structure of the macrophage signal regulatory protein alpha (SIRPalpha) inhibitory receptor reveals a binding face reminiscent of that used by T cell receptors", J Biol Chem. 282(19), 2007, 14567-14575.
Huang, et al., "CTLA-4-Fas ligand functions as a trans signal converter protein in bridging antigen-presenting cells and T cells", Int Immunol. 13(4), 2001, 529-539.
Jaiswal, et al., "CD47 is upregulated on circulating hematopoietic stem cells and leukemia cells to avoid phagocytosis". Cell. 138(2), 2009, 271-285.
Lee, et al., "The role of cis dimerization of signal regulatory protein alpha (SIRPalpha) in binding to CD47", J Biol Chem. 285(49), 2010, 37953-37963.
Lensink, et al., "Docking and scoring protein complexes: CAPRI 3rd Edition", Proteins. 69(4), 2007, 704-718.
Majeti, et al., "CD47 is an adverse prognostic factor and therapeutic antibody target on human acute myeloid eukemia stem cells", Cell. 138(2), 2009, 286-299.

(Continued)

*Primary Examiner* — Brad Duffy
(74) *Attorney, Agent, or Firm* — Saul Ewing Arnstein & Lehr LLP; Kathryn Doyle

(57) ABSTRACT

Provided is a fusion protein comprising a polypeptide component that blocks binding of CD47 to SIRP alpha and a polypeptide that binds to and triggers a TRAIL receptor or Fas. Also provided is a method of treating cancer in a patient comprising administering the fusion protein of the invention to a patient in need of such treatment.

9 Claims, 1 Drawing Sheet
Specification includes a Sequence Listing.

(56) References Cited

OTHER PUBLICATIONS

Nilsson, et al., "CD47 promotes both phosphatidylserine-independent and phosphatidylserine-dependent phagocytosis of apoptotic murine thymocytes by non-activated macrophages", Biochem Biophys Res Commun. 387 (1), 2009, 58-63.
Orbach, et al., "CD40-FasL and CTLA-4-FasL fusion proteins induce apoptosis in malignant cell lines by dual signaling", Am J Pathol. 177(6), 2010, 3159-3168.
Schneider, et al., "Potent antitumoral activity of TRAIL through generation of tumor-targeted single-chain fusion proteins", Cell Death Dis. 1, 2010, e68.
Sissoeff, et al., "Stable trimerization of recombinant rabies virus glycoprotein ectodomain is required for interaction with the p75NTR receptor", J Gen Virol. 86(Pt 9), 2005, 2543-2552.
Stefanidakis, et al., "Endothelial CD47 interaction with SIRPgamma is required for human T-cell transendothelial migration under shear flow conditions in vitro", Blood. 112(4), 2008, 1280-1289.
Tame, "Scoring functions: a view from the bench", J Comput Aided Mol Des. 13(2), 1999, 99-108.
Theocharides, et al., "Disruption of SIRPα signaling in macrophages eliminates human acute myeloid leukemia stem cells in xenografts", J Exp Med. 209(10), 2012, 1883-1899.
Willingham, et al., "The CD47-signal regulatory protein alpha (SIRPa) interaction is a therapeutic target for human solid tumors", Proc. Natl. Acad Sci. U S A 109, 2012, 6662-6667.

\* cited by examiner

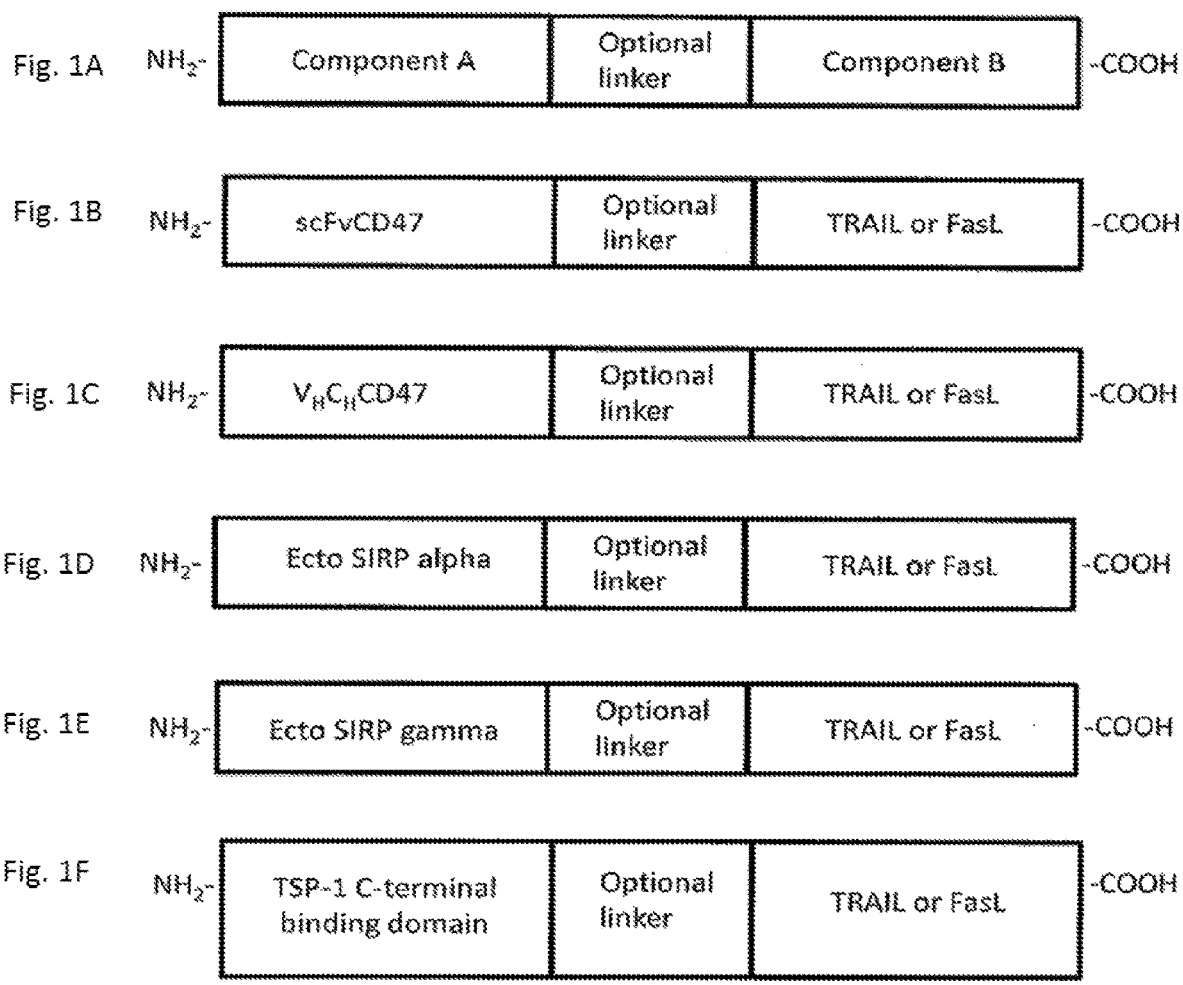

FUSION PROTEINS THAT FACILITATE CANCER CELL DESTRUCTION

CROSS REFERENCE TO RELATED APPLICATIONS

This application is a continuation of, and claims priority to, U.S. patent application Ser. No. 14/763,701, filed Jul. 27, 2015, now U.S. Pat. No. 9,873,747, which is a 35 U.S.C. § 371 national phase application from, and claims priority to, International Application No. PCT/US2014/014189, filed Jan. 31, 2014, and published under PCT Article 21(2) in English, which, claims the benefit of U.S. Provisional Application No. 61/759,301 filed Jan. 31, 2013, all of which applications are incorporated herein by reference in their entireties.

FIELD OF THE INVENTION

The present invention relates to fusion proteins comprising a component that blocks CD47 binding to its cognate receptor and a component comprising an apoptosis-inducing protein.

BACKGROUND OF THE INVENTION

CD47 is expressed on the surface of all human solid tumors. CD47 mRNA expression levels correlated with a decreased probability of survival for multiple types of cancer. CD47 is a ligand for SIRP alpha, a cell surface receptor expressed on macrophages. Binding of CD47 to SIRP alpha suppresses macrophage phagocytosis of tumor cells. Thus, CD47 has been dubbed a "don't eat me" signal. See, e.g., Willingham et al., (2012) *Proc. Natl. Acad. Sci. USA* (Published online before print Mar. 26, 2012, doi: 10.1073/pnas. 1121623109.)

Anti-CD47 antibody therapy has been proposed as a new therapeutic approach for treating solid tumors. Anti-CD47 antibodies bind CD47 and hinder or prevent the binding of CD47 to SIRP alpha on macrophages. Thus, the "don't eat me" signal would be squelched. Preliminary work has suggested this therapeutic path has promise. However, concerns about specificity and adverse side effects have arisen.

There is a need in the art for improved therapeutic agents for treating solid tumors.

SUMMARY OF THE INVENTION

Provided is a fusion protein comprising Component A and Component B, wherein Component A comprises a CD47 blocker and Component B comprise a polypeptide that binds to and triggers a TRAIL receptor or Fas, and optionally comprising a linker between Components A and B. In some embodiments, the N-terminus of Component A is fused to the C-terminus of Component B, either directly or indirectly via the linker. In some embodiments, the CD47 blocker comprises at least a portion of the ectodomain of SIRP alpha. In other embodiments, the CD47 blocker comprises at least a portion of the ectodomain of SIRP gamma. In yet other embodiments, the CD47 blocker comprises at least a portion of the cell binding domain of thrombospondin-1. In further embodiments, the CD47 blocker comprises a derivative of a monoclonal anti-CD47 antibody, the derivative selected from scFvCD47, VHCHCD47, and VHHCD47.

In further embodiments, Component B comprises human TRAIL, or a fragment thereof. In other embodiments, Component B comprises human Fas ligand, or a fragment thereof.

In further embodiments, the fusion protein comprises at least a portion of SEQ ID NO: 1, SEQ ID NO: 2, SEQ ID NO: 3, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, or SEQ ID NO: 14.

In one embodiment, the fusion protein comprises SEQ ID NO: 13. In another embodiment, the fusion protein comprises SEQ ID NO: 14.

In any of the embodiments, the fusion protein may further comprise a trimerization domain.

In any of the preceding embodiments, the fusion protein may consist essentially of Component A, Component B, optionally comprising a linker between Components A and B, and optionally comprising a trimerization domain. In a further embodiment, the fusion protein may consist essentially of Component A, Component B, optionally comprising a linker between Components A and B.

In any embodiments wherein the fusion protein comprises a linker, the linker may comprise one of SEQ ID NO: 17, SEQ ID NO: 19 and SEQ ID NO: 20.

Also provided is a pharmaceutical composition comprising a pharmaceutically acceptable carrier and the fusion protein of any of the embodiments disclosed herein.

A method of treating a proliferative disorder in a patient is also provided. The method comprises administering an therapeutically effective amount of the fusion protein of any of the embodiments disclosed herein to a patient in need of such treatment. In some embodiments, the proliferative disorder is cancer. In some embodiments, the cancer is a solid tumor. In some embodiments, the cancer is one of pancreatic cancer, breast cancer, ovarian cancer, bladder cancer, melanoma, glioblastoma, acute lymphoblastic leukemia (ALL) and acute myelogenous leukemia (AML).

Further provided is a fusion protein of any of the preceding embodiments or any embodiment disclosed herein, for use (i) in medicine, (ii) treating a proliferative disorder, or (iii) treating cancer. Provided is a genetic sequence encoding a fusion protein of any one of the preceding embodiments, for use in medicine, or for use in treating a proliferative disorder, such as cancer.

BRIEF DESCRIPTION OF THE DRAWINGS

FIGS. 1A-1F are series of schematic drawings depicting various embodiments of the fusion protein of the invention. FIG. 1A: In an embodiment, the fusion protein comprises Component A fused to Component B with an optional linker. FIG. 1B: In an embodiment, the fusion protein comprises scFvCD47 fused to TRAIL or FasL, or a fragment thereof, with an optional linker. FIG. 1C: In an embodiment, the fusion protein comprises $V_HC_HCD47$ fused to TRAIL or FasL, or a fragment thereof, with an optional linker. FIG. 1D: In an embodiment, the fusion protein comprises at least a portion of the ectodomain of SIRP alpha fused to TRAIL or FasL, or a fragment thereof, with an optional linker. FIG. 1E: In an embodiment, the fusion protein comprises at least a portion of the ectodomain of SIRP gamma fused to TRAIL or FasL, or a fragment thereof, with an optional linker. FIG. 1F: In an embodiment, the fusion protein comprises TSP-1 C-terminal binding domain fused to TRAIL or FasL, or a fragment thereof, with an optional linker.

DEFINITIONS

As used in the specification and the appended claims, the singular forms "a," "an" and "the" include plural referents unless the context clearly dictates otherwise.

The term "about" will be understood by persons of ordinary skill in the art and will vary to some extent depending on the context in which it is used. As used herein, "about" is meant to encompass variations of ±20% or ±10%, more preferably ±5%, even more preferably ±1%, and still more preferably ±0.1%.

A "fusion protein" or "fusion polypeptide" is a polypeptide comprised of at least two polypeptides and optionally a linking sequence, and that are operatively linked into one continuous protein. The two polypeptides linked in a fusion protein are typically derived from two independent sources, and therefore a fusion protein comprises two linked polypeptides not normally found linked in nature. Typically, the two polypeptides can be operably attached directly by a peptide bond.

The term "operably linked," as used herein, indicates that two molecules (e.g., polypeptides) are attached so as to each retain biological activity. Two molecules are "operably linked" whether they are attached directly or indirectly (e.g., via a linker).

The term "linker" as used herein refers to a peptide that is optionally located between two amino acid sequences in the fusion protein of the invention.

As used herein, a "biologically active" or an "immunologically active" as applied to a fusion protein refers to a fusion protein according to the present invention having a similar structural function (but not necessarily to the same degree), and/or similar regulatory function (but not necessarily to the same degree), and/or similar biochemical function (but not necessarily to the same degree) and/or immunological activity (but not necessarily to the same degree) as the individual wild-type proteins which are the building blocks of the fusion protein.

As used herein, "CD47" refers to a cell surface transmembrane protein that is widely expressed on normal cells as well as all human solid tumor cells. CD47 has a single IgGv extracellular domain, five transmembrane segments, and a short COOH-terminal cytoplasmic tail. CD47 is a ligand for SIRP alpha, by way of its extracellular domain. Other names in the art for CD47 include: integrin-associate protein, IAP, MER6 and OA3. There are several splice variants for human CD47. For at least variants 1, 2 and 3, the first 303 amino acids are identical. An exemplary protein sequence for human CD47 is GENBANK® Accession no. NP_001768.1 (sequence includes signal peptide), which is encoded by nucleic acid sequence GENBANK® Accession no. NM_0017773.

As used herein, "SIRP alpha" refers to a cell surface type I transmembrane protein that is expressed on macrophages and is member of the SIRP/SHPS (CD172) family within the Ig superfamily. SIRP alpha is a receptor for CD47. Other names in the art for SIRP alpha include: signal regulatory protein alpha, tyrosine-protein phosphatase non-receptor type substrate 1, BIT, CD172A, MFR, MYD-1, P84, PTPNS1, and SHPS1. An exemplary protein sequence for human SIRP alpha is GENBANK® Accession no. AAH33092.1 (sequence includes signal peptide), which is encoded by nucleic acid sequence GENBANK® Accession no. BC033092.1.

As used herein, "SIRP gamma" refers to a cell surface type I transmembrane protein that is another member of the SIRP/SHPS (CD172) family within the Ig superfamily and expressed, for instance, on T cells and activated NK cells. SIRP gamma can bind CD47 but a signaling mechanism is not known. Other names in the art for SIRP alpha include: signal regulatory protein gamma, and SIRP beta 2. An exemplary protein sequence for human SIRP gamma is GENBANK® Accession no. NP_061026.2 (sequence includes signal peptide), which is encoded by nucleic acid sequence GENBANK® Accession no. NM_018556.3.

As used herein, "thrombospondin-1" refers to a multi-domain matrix glycoprotein. Other names in the art for thrombospondin-1 include: TSP-1 and THBS1. The globular C-terminal portion of TSP-1 comprising the sequence RFYVVMWK (SEQ ID NO: 24) is the cell binding domain of thrombospodin-1 ("TSP-1 CBD") and it binds to CD47. An exemplary protein sequence for human thrombospondin-1 is GENBANK® Accession no. NP_003237.2 (sequence includes signal peptide), which is encoded by nucleic acid sequence GENBANK® Accession no. NM_003246.2.

The term "TRAIL receptor" as used herein refers to a receptor that binds to TRAIL ligand and induces or triggers apoptosis. In some embodiments, the TRAIL receptor is DR4 (TRAILR1). In some embodiments, the TRAIL receptor is DR5 (TRAILR2). The term "TRAIL receptor" as used herein does not refer to the receptors DcR1 (TRAILR3) and DcR2. DcR1 does not contain a cytoplasmic domain, and DcR2 (TRAILR4) contains a truncated death domain. DcR1 functions as a TRAIL-neutralizing decoy-receptor. The cytoplasmic domain of DcR2 is functional and activates NFkappaB. In cells expressing DcR2, TRAIL binding therefore activates NFkappaB, leading to transcription of genes known to antagonize the death signaling pathway and/or to promote inflammation.

The term "Fas" or "Fas receptor" as used herein refers to a receptor that binds to Fas ligand (FasL) and induces or triggers apoptosis.

As used here, "trigger" with respect to a receptor, such as SIRP alpha, refers to the biological change that occurs upon ligation of the receptor by an agonist ligand. Biological changes that can occur when a receptor is triggered include, but are not limited to, one or more of: receptor interaction with one or more intracellular adaptors and effector molecules; induction of a signaling cascade; modified expression of molecules; release of cytokines and/or chemokines; activation of caspases; activation of transcription factors; changes in protein modification such as a phosphorylation; activation of signal transduction pathways such as NF-κB and P13K; induction of downstream effects on transcriptional, translational, and post-translational control mechanisms affecting one or more genes and/or proteins expressed by the cell.

The term "CD47 blocker" in particular includes any entity that either prevents the binding of CD47 to SIRP alpha, or permits binding but prevents the triggering of SIRP alpha. This includes CD47 antibodies and fragments thereof; and soluble fragments of SIRP alpha, soluble fragments of SIRP gamma, and the C-terminal binding domain of thrombospondin-1, and fragments and derivatives thereof.

The term "antibody," as used herein, refers to an immunoglobulin molecule which is able to specifically bind to a specific epitope on an antigen, as well as fragments and derivatives of thereof, which fragments and derivatives have at least an antigenic binding site. Antibodies can be intact immunoglobulins derived from natural sources or from recombinant sources and can be immunoreactive portions of intact immunoglobulins. Antibodies are typically tetramers of immunoglobulin molecules. Antibodies may exist in a variety of forms including, for example, polyclonal antibodies, monoclonal antibodies, intracellular antibodies ("intrabodies"), Fv, Fab and F(ab)$_2$, as well as single chain antibodies (scFv), heavy chain antibodies such as camelid antibodies, chimeric antibodies, and humanized antibodies (Harlow et al., 1999, *Using Antibodies: A Laboratory Manual*, Cold Spring Harbor Laboratory Press, NY; Harlow et al., 1989, *Antibodies: A Laboratory Manual*, Cold Spring Harbor, N.Y.; Houston et al., 1988, *Proc. Natl. Acad. Sci. USA* 85:5879-5883; Bird et al., 1988, *Science* 242:423-426).

The term "humanized" when used in reference to an antibody, means that the amino acid sequence of the antibody has non-human amino acid residues (e.g., mouse, rat, goat, rabbit, etc.) of one or more complementarity determining regions (CDRs) that specifically bind to the desired antigen in an acceptor human immunoglobulin molecule, and one or more human amino acid residues in the Fv framework region (FR), which are amino acid residues that flank the CDRs. Such antibodies typically have reduced immunogenicity and therefore a longer half-life in humans as compared to the non-human parent antibody from which one or more CDRs were obtained or are based upon.

The term "chimeric" and grammatical variations thereof, when used in reference to an antibody, means that the amino acid sequence of the antibody contains one or more portions that are derived from, obtained or isolated from, or based upon two or more different species. For example, a portion of the antibody may be human (e.g., a constant region) and another portion of the antibody may be non-human (e.g., a murine heavy or murine light chain variable region). Thus, an example of a chimeric antibody is an antibody in which different portions of the antibody are of different species origins. Unlike a humanized or primatized antibody, a chimeric antibody can have the different species sequences in any region of the antibody.

As used herein, the term "anti-CD47 antibody" means an antibody that specifically binds to a CD47 molecule, such as human CD47, and reduces binding of CD47 to SIRP alpha by at least about 20% when added to a cell, tissue or organism expressing CD47 and SIRP alpha. In some embodiments, the antibody inhibits CD47 binding activity by at least 40%, 50%, 60%, 70%, 80%, or 85%.

A polypeptide having an "ectodomain" is one wherein a portion of the polypeptide is positioned within a cellular membrane and a portion of the polypeptide is located on the outside of a cell. Typically, the polypeptide spans the cell membrane of a cell. Thus, by the term "ectodomain" of a polypeptide is meant that portion of a polypeptide which is located on the outside of a cell (i.e., extracellular domain), where another portion of the polypeptide spans or is otherwise located within the cell membrane.

As used herein, a "deletion" in an amino acid sequence or polypeptide is defined as a change in amino acid sequence in which one or more amino acid residues are absent as compared to the wild-type protein.

As used herein an "insertion" or "addition" in an amino acid sequence or polypeptide is a change in an amino acid sequence that has resulted in the addition of one or more amino acid residues as compared to the wild-type protein.

As used herein "substitution" in an amino acid sequence or polypeptide results from the replacement of one or more amino acids by different amino acids, respectively, as compared to the wild-type protein.

As used herein, a "trimerization domain" refers to an amino acid sequence within a polypeptide that promotes assembly of the polypeptide into trimers. For example, a trimerization domain can promote assembly of a protein into trimers via associations with other trimerization domains (of additional polypeptides with the same or a different amino acid sequence). The term is also used to refer to a polynucleotide that encodes such a peptide or polypeptide.

As used herein, the term "variant" with respect to an amino acid sequence or polypeptide means any polypeptide having a substitution of, deletion of or addition of one (or more) amino acid from or to the sequence, including allelic variations, as compared with the wild-type protein, so long as the resultant variant fusion protein retains at least 75%, 80%, 85%, 90%, 95%, 96%, 97%, 98%, 99% or more of the biological or immunologic activity as compared to the wild-type proteins as used in the present invention. Additionally, while in general it is desirable for variants to show enhanced ability for binding to a given molecule, in some embodiments variants may be designed with slightly reduced activity as compared to other fusion proteins of the invention, for example, in instances in which one would purposefully want to attenuate activity.

Sequence identity or homology can be determined using standard techniques known in the art, such as the Best Fit sequence program described by Devereux et al., *Nucl. Acid Res.* 12:387-395 (1984) or the BLASTX program (Altschul et al., *J. Mol. Biol.* 215, 403-410). The alignment may include the introduction of gaps in the sequences to be aligned. In addition, for sequences which contain either more or fewer amino acids than the proteins disclosed herein, it is understood that the percentage of homology will be determined based on the number of homologous amino acids in relation to the total number of amino acids.

Preferably, variants or derivatives of the fusion proteins of the present invention maintain the hydrophobicity/hydrophilicity of the parent amino acid sequence. Conservative amino acid substitutions may be made, for example from 1, 2 or 3 to 10, or 30 substitutions provided that the modified sequence retains the ability to act as a fusion protein in accordance with present invention. Amino acid substitutions may include the use of non-naturally occurring analogues, for example to increase blood plasma half-life.

Conservative substitutions are known in the art, for example according to the table below. Amino acids in the same block in the second column and preferably in the same line in the third column may be substituted for each other:

| ALIPHATIC | Non-polar | GAPILV |
|---|---|---|
|  | Polar- | CSTM |
|  | Uncharged | NQ |
|  | Polar-charged | DE |
|  |  | KR |
| AROMATIC |  | HFWY |

The term "derivative" as used herein in relation to an amino acid sequence means chemical modification of a fusion protein of the invention.

The term "derivative" in the context of an antibody refers to a portion of an immunoglobulin having at least an antigenic binding site. Examples include but are not limited to intracellular antibodies ("intrabodies"), Fv, Fab and F(ab)$_2$, as well as single chain antibodies (scFv), heavy chain antibodies such as camelid antibodies, chimeric antibodies, and humanized antibodies.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

As used herein "endogenous" refers to any material from or produced inside an organism, cell, tissue or system.

As used herein, the term "exogenous" refers to any material introduced from or produced outside an organism, cell, tissue or system.

The term "expression" as used herein is defined as the transcription and/or translation of a particular nucleotide sequence driven by its promoter.

The term "expression vector" as used herein refers to a vector containing a nucleic acid sequence coding for at least part of a gene product capable of being transcribed. In some cases, RNA molecules are then translated into a protein, polypeptide, or peptide. Expression vectors can contain a variety of control sequences, which refer to nucleic acid sequences necessary for the transcription and possibly translation of an operatively linked coding sequence in a particular host organism. In addition to control sequences that govern transcription and translation, vectors and expression vectors may contain nucleic acid sequences that serve other functions as well.

An "isolated nucleic acid" refers to a nucleic acid segment or fragment which has been separated from sequences which flank it in a naturally occurring state, i.e., a DNA fragment which has been removed from the sequences which are normally adjacent to the fragment, i.e., the sequences adjacent to the fragment in a genome in which it naturally occurs. The term also applies to nucleic acids which have been substantially purified from other components which naturally accompany the nucleic acid, i.e., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (i.e., as a cDNA or a genomic or cDNA fragment produced by PCR or restriction enzyme digestion) independent of other sequences. It also includes a recombinant DNA which is part of a hybrid gene encoding additional polypeptide sequence.

In the context of the present invention, the following abbreviations for the commonly occurring nucleic acid bases are used, "A" refers to adenosine, "C" refers to cytosine, "G" refers to guanosine, "T" refers to thymidine, and "U" refers to uridine.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

The term "polynucleotide" as used herein is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and PCR™, and the like, and by synthetic means.

The term "polypeptide" as used herein is defined as a chain of amino acid residues, usually having a defined sequence. As used herein the term polypeptide is mutually inclusive of the terms "peptide" and "protein."

As used herein, a polypeptide is "soluble" when it lacks any transmembrane domain or peptide domain that anchors or integrates the polypeptide into the membrane of a cell expressing such polypeptide. In particular, the soluble proteins useful as components in the fusion protein of the invention may exclude transmembrane and intracellular domains. The soluble proteins may comprise substantially all of an ectodomain or may comprise a fragment thereof possessing the required agonist function, e.g., a functional fragment.

The term "promoter" as used herein is defined as a DNA sequence recognized by the synthetic machinery of the cell, or introduced synthetic machinery, required to initiate the specific transcription of a polynucleotide sequence.

As used herein, the term "promoter/regulatory sequence" means a nucleic acid sequence which is required for expression of a gene product operably linked to the promoter/regulatory sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

A "constitutive" promoter is a nucleotide sequence which, when operably linked with a polynucleotide which encodes or specifies a gene product, causes the gene product to be produced in a cell under most or all physiological conditions of the cell.

An "inducible" promoter is a nucleotide sequence which, when operably linked with a polynucleotide which encodes or specifies a gene product, causes the gene product to be produced in a cell substantially only when an inducer which corresponds to the promoter is present in the cell.

A "tissue-specific" promoter is a nucleotide sequence which, when operably linked with a polynucleotide which encodes or specifies a gene product, causes the gene product to be produced in a cell substantially only if the cell is a cell of the tissue type corresponding to the promoter.

The term "RNA" as used herein is defined as ribonucleic acid.

The term "recombinant DNA" as used herein is defined as DNA produced by joining pieces of DNA from different sources.

The term "recombinant polypeptide" as used herein is defined as a polypeptide produced by using recombinant DNA methods.

As used herein, a "therapeutically effective amount" is the amount of a composition sufficient to provide a beneficial effect to a mammal to which the composition is administered. An therapeutically effective amount of a composition of the invention is an amount that will ameliorate one or more of the well-known parameters that characterize medical conditions caused by a proliferative disorder, for instance, a tumor. Many such parameters and conditions have been described and are well known to the skilled artisan. A therapeutically effective amount, in the context of a proliferative disorder, such as a tumor, will be the amount of fusion protein that is sufficient to accomplish one or more of the following: decrease the severity of symptoms; decrease tumor size; decrease rate of tumor growth; increase the frequency and duration of disease remission/symptom-free periods; and/or prevent/attenuate chronic progression of the disease.

The term "transfected" or "transformed" or "transduced" as used herein refers to a process by which exogenous nucleic acid is transferred or introduced into the host cell. A "transfected" or "transformed" or "transduced" cell is one that has been transfected, transformed or transduced with exogenous nucleic acid. The cell includes the primary subject cell and its progeny.

The phrase "under transcriptional control" or "operatively linked" as used herein with respect to polynucleotides means that the promoter is in the correct location and orientation in relation to a polynucleotide to control the initiation of transcription by RNA polymerase and expression of the polynucleotide.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, adenoviral vectors, adeno-associated virus vectors, retroviral vectors, and the like.

As used herein in the specification and claims, including as used in the examples and unless otherwise expressly specified, all numbers may be read as if prefaced by the word "about," even if the term does not expressly appear.

Ranges: Throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Where any amino acid sequence is specifically referred to by a Swiss Prot. or GENBANK® Accession number, the sequence is incorporated herein in its entirety by reference. Information associated with the accession number, such as identification of signal peptide, extracellular domain, transmembrane domain, promoter sequence and translation start, is also incorporated herein in its entirety by reference.

As envisioned in the present invention with respect to the disclosed compositions of matter and methods, in one aspect, the embodiments of the invention comprise the components and/or steps disclosed therein. In another aspect, the embodiments of the invention consist essentially of the components and/or steps disclosed therein. In yet another aspect, the embodiments of the invention consist of the components and/or steps disclosed therein.

DETAILED DESCRIPTION OF THE INVENTION

The present invention provides a fusion protein comprising as Component A a polypeptide that binds to CD47 and inhibits or reduces its binding to SIRP alpha, and, as Component B, a polypeptide that binds to and triggers a TRAIL receptor or binds to and triggers a Fas receptor. In particular, the Component A comprises a CD47 blocker, and Component B comprises at least a portion of a polypeptide that can bind to TRAIL receptor or Fas receptor and direct inhibitory signals, including pro-apoptotic ones, through cognate receptors on T cells or other cells bearing a TRAIL receptor or a Fas receptor.

The present invention provides novel fusion proteins useful for treating proliferative disorders, such as cancer. In the setting of cancer, the fusion protein of this invention can inhibit or prevent a tumor cell's evasion of phagocytosis, for instance, by macrophages, and trigger an apoptosis-inducing receptor. Thus, on a cell co-expressing CD47 and an activated TRAIL or Fas receptor, the fusion protein of the invention may lead to death and clearance of the tumor cell by two mechanisms.

Alternatively, the fusion protein of the present invention may mediate its activity by spanning two neighboring cells. For example, the fusion protein of the invention can bind to a CD47-expressing tumor cells, thereby interfering with its ability to bind to SIRP alpha and prevent phagocytosis. In addition, the apoptosis-inducing TRAIL ligand or Fas ligand component of the fusion protein of the invention, now membrane-anchored, can bind to a neighboring tumor cell expressing an activated TRAIL receptor or Fas L receptor, thus triggering apoptosis in the neighboring cell. Thus, the fusion proteins act to treat disease by causing a reduction in certain cells.

Component A: CD47 Blocker

Suitable polypeptides to act as a CD47 blocker include, for example, soluble fragments of polypeptides that bind CD47 in vivo. Such polypeptides include: SIRP alpha, SIRP gamma, thrombospondin-1, and functional fragments thereof. Other suitable polypeptides to act as a CD47 blocker are anti-CD47 antibodies, and antibody derivatives comprising functional fragments thereof.

In a preferred embodiment, Component A comprises a functional fragment of SIRP alpha, or a functional fragment thereof. Preferably, the functional fragment of SIRP alpha is a soluble form ("sSIRP alpha"), such as the ectodomain of SIRP alpha, or a biologically active fragment thereof. As used herein, the term "biological active fragment thereof" in the context of the ectodomain of SIRP alpha encompasses any fragment of the ectodomain that can specifically bind to CD47 and inhibit CD47 binding to SIRP alpha, for example, on a macrophage.

SIRP alpha is a Type I membrane protein and has been sequenced in a number of species, including, but not limited to, mouse: GENBANK® Accession no. AAH62197.1; Human: GENBANK® Accession no. AAH33092. 1; *Pan troglodytes* (chimpanzee): GENBANK® Accession no. JAA10535.1; *Macaca mulatta* (rhesus monkey): GENBANK® Accession no. AFE76783.1; Gorilla gorilla gorilla (Western lowland gorilla): GENBANK® Accession no. XP_004061735.1; and *Bos taurus*: GENBANK® Accession no. NP_786982.1.

Human SIRP alpha has 503 amino acids. An exemplary sequence for the ectodomain of human SIRP alpha comprises or consists of:

(SEQ ID NO: 1)
GVAGEEELQVIQPDKSVLVAAGETATLRCTATSLIPVGPIQWFRGAG

PGRELIYNQKEGHFPRVTTVSDLTKRNNMDFSIRIGNITPADAGTYY

CVKFRKGSPDDVEFKSGAGTELSVRAKPSAPVVSGPAARATPQHTVS

FTCESHGFSPRDITLKWFKNGNELSDFQTNVDPVGESVSYSIHSTAK

VVLTREDVHSQVICEVAHVTLQGDPLRGTANLSETIRVPPTLEVTQQ

PVRAENQVNVTCQVRKFYPQRLQLTWLENGNVSRTETASTVTENKDG

TYNWMSWLLVNVSAHRDDVKLTCQVEHDGQPAVSKSHDLKVSAHPKE

QGSNTAAENTGSNERNIY.

SEQ ID NO: 1 constitutes residues 27-373 of the human SIRP alpha polypeptide sequence in GENBANK® Accession No. AAH33092.1.

Another exemplary sequence for the ectodomain of human SIRP alpha comprises or consists of:

(SEQ ID NO: 2)
GEEELQVIQPDKSVLVAAGETATLRCTATSLIPVGPIQWFRGAGPGR

ELIYNQKEGHFPRVTTVSDLTKRNNMDFSIRIGNITPADAGTYYCVK

FRKGSPDDVEFKSGAGTELSVRAKPSAPVVSGPAARATPQHTVSFTC

ESHGFSPRDITLKWFKNGNELSDFQTNVDPVGESVSYSIHSTAKVVL

TREDVHSQVICEVAHVTLQGDPLRGTANLSETIRVPPTLEVTQQPVR

AENQVNVTCQVRKFYPQRLQLTWLENGNVSRTETASTVTENKDGTYN

WMSWLLVNVSAHRDDVKLTCQVEHDGQPAVSKSHDLKVSAHPKEQGS

NTAAENTGSNER.

In some embodiments, the CD47 blocker comprises the ectodomain of human SIRP alpha. In other embodiments, the CD47 blocker comprises a fragment of human SIRP alpha comprising at least 20, 30, 40, 50, 60, 70, 80, 90, 100, 110, 120, 130, 140, 150, 160, 170, 180, up to 508 contiguous amino acids of the full-length SIRP alpha protein, wherein the fragment specifically binds to CD47 and inhibits CD47 binding to SIRP alpha, for instance, on a macrophage.

SIRP alpha fragments that can act as CD47 blockers are also known in the art. See, e.g., Hatherley et al., (2007), *The Journal of Biological Chemistry*, 282, 14567-14575 (First Published on Mar. 16, 2007, doi: 10.1074/jbc.M611511200 May 11, 2007). Hatherley et al. teach a fragment comprising residues 1-148 of Genbank® accession no. CAA71403, wherein the N-terminus amino acid sequence of the mature fragment is expected to be EEEL.

In a preferred embodiment, Component A comprises a functional fragment of SIRP gamma, or a functional fragment thereof. Preferably, the functional fragment of SIRP gamma is a soluble form ("sSIRP gamma"), such as the ectodomain of SIRP gamma, or a biologically active fragment thereof. As used herein, the term "biological active fragment thereof" in the context of the ectodomain of SIRP gamma encompasses any fragment of the ectodomain that can specifically bind to CD47 and inhibits CD47 binding to SIRP alpha, for example, on a macrophage. An exemplary sequence for an ectodomain of human SIRP gamma is residues 26 to 357 of the polypeptide sequence of GENBANK® Accession No. NP_061026.2.

An exemplary sequence for the ectodomain of human SIRP gamma comprises or consists of:

(SEQ ID NO: 3)
VAGEEELQMIQPEKLLLVTVGKTATLHCTVTSLLPVGPVLWFRGVGP

GRELIYNQKEGHFPRVTTVSDLTKRNNMDFSIRISSITPADVGTYYC

VKFRKGSPENVEFKSGPGTEMALGAKPSAPVVLGPAARTTPEHTVSF

TCESHGFSPRDITLKWFKNGNELSDFQTNVDPTGQSVAYSIRSTARV

VLDPWDVRSQVICEVAHVTLQGDPLRGTANLSEAIRVPPTLEVTQQP

MRVGNQVNVTCQVRKFYPQSLQLTWSENGNVCQRETASTLTENKDGT

YNWTSWFLVNISDQRDDVVLTCQVKHDGQLAVSKRLALEVTVHQKDQ

SSD.

In some embodiments, the CD47 blocker comprises the ectodomain of human SIRP gamma. In other embodiments, the CD47 blocker comprises a fragment of human SIRP gamma comprising at least 20, 30, 40, 50, 60, 70, 80, 90, 100, 110, 120, 130, 140, 150, 160, 170, 180, up to 387 contiguous amino acids of the full-length SIRP gamma protein, wherein the fragment specifically bind to CD47 and inhibit CD47 binding to SIRP alpha, for instance, on a macrophage.

In another embodiment, Component A comprises the cell-binding domain of thrombospondin-1 (TSP-1 CBD). The globular C-terminal portion of TSP-1 comprising the sequence RFYVVM (SEQ ID NO: 24) is the cell binding domain of thrombospodin-1 ("TSP-1 CBD") and it binds to CD47. TSP-1 CBD sequences are known in the art. See, e.g., Brown et al., 2001, "Integrin-associated protein (CD47) and its ligands," *Trends in Cell Biology* 11(3): 130-135; and Floquet et al., 2008, "Human thrombospondin's (TSP-1) C-terminal domain opens to interact with the CD-47 receptor: A molecular modeling study," *Archives of Biochemistry and Biophysics,* 478 (1): 103-109.

In some embodiments, the CD47 blocker comprises about the C-terminal 212 amino acids of human TSP-1. In other embodiments, the CD47 blocker comprises a fragment of human TSP-1 comprising at least 20, 30, 40, 50, 60, 70, 80, 90, 100, 110, 120, 130, 140, 150, 160, 170, 180, up to 1169 contiguous amino acids of the full-length TSP-1 protein, wherein the fragment comprises SEQ ID NO: 24 and specifically binds to CD47 and inhibits CD47 binding to SIRP alpha, for instance, on a macrophage.

In another embodiment, Component A comprises an antibody derivative of a monoclonal anti-CD47 antibody. In an embodiment, the CD47 blocker is a single chain variable fragment (scFv) comprising a $V_H$ domain and a $V_L$ domain from a monoclonal anti-CD47 antibody. This antibody derivative is referred to herein as "scFvCD47." In another embodiment, the CD47 blocker comprises a $V_H$ domain and heavy chain constant region from a monoclonal anti-CD47 antibody. This antibody derivative is referred to herein as "$V_H C_H$CD47." For embodiments wherein the CD47 blocker comprises $V_H C_H$CD47, a polypeptide comprising a $V_L$ domain and light chain constant region from the monoclonal anti-CD47 antibody, referred to herein as "$V_L C_L$CD47," is optionally provided in trans.

Anti-CD47 antibodies are known in the art. For instance, Jaiswal et al. (U.S. Pat. Appln. Pub. 2001/0014119) teach monoclonal antibodies against human CD47. Jaiswal et al.

teach an exemplary fragment of the ectodomain of CD47 useful for preparing monoclonal antibodies. See also Willingham et al., (2012), *Proc. Natl. Acad. Sci. USA*. (Published online before print Mar. 26, 2012, doi: 10. 1073/pnas. 1121623109).

In another embodiment, the CD47 blocker is a $V_HH$ (camelid heavy chain antibody); this antibody form is referred to herein as "$V_H$HCD47."

Monoclonal antibodies against non-human CD47 may also be used in the invention, provided they bind and inhibit binding of CD47 to SIRP alpha in the recipient of the fusion protein.

The skilled artisan can make monoclonal antibodies to CD47 using conventional methods described elsewhere herein. A suitable antigen for preparing monoclonal antibodies is the ectodomain of CD47. An exemplary sequence for the ectodomain of human CD47 comprises or consists of:

```
(SEQ ID NO: 4; residues 9 to 142 of NP_001768.1)
LGSACCGSAQLLFNKTKSVEFTFCNDTVVIPCFVTNMEAQNTTEVYVK

WKFKGRDIYTFDGALNKSTVPTDFSSAKIEVSQLLKGDASLKMDKSDA

VSHTGNYTCEVTELTREGETIIELKYRVVSWFSPNEN.
```

Another exemplary sequence for the ectodomain of human CD47 comprises or consists of:

```
                                      (SEQ ID NO: 5)
QLLFNKTKSVEFTFCNDTVVIPCFVTNMEAQNTTEVYVKWKFKGRDIY

TFDGALNKSTVPTDFSSAKIEVSQLLKGDASLKMDKSDAVSHTGNYTC

EVTELTREGETIIELKYRVVSWFSPNEN.
```

Methods of assessing whether a monoclonal antibody against CD47 has the function of inhibiting binding to SIRP alpha are known in the art. Exemplary methods include, but are not limited to, assaying a candidate monoclonal CD47 antibody's ability to inhibit activation of SIRP alpha on macrophages and inhibition of SIRP alpha tyrosine phosphorylation activity. See, for instance, Jaiswal et al. (U.S. Pat. Appln. Pub. 2001/0014119).

Component B: TRAIL

In one embodiment of the fusion protein of the invention, Component B comprises TRAIL. TRAIL is a Type II membrane protein having 281 amino acids and has been sequenced in a number of species, including, but not limited to, mouse: Swiss Prot. Accession No. P50592: human: Swiss Prot. Accession No. P50591; *Rattus norvegicus*: NCBI Accession NP_663714; *Siniperca chuatsi* (Chinese Perch): NCBI Accession AAX77404; *Gallus gallus* (Chicken): NCBI Accession BAC79267; *Sus scrofa* (Pig): NCBI Accession NP_001019867; *Ctenopharyngodon idella* (Grass Carp): NCBI Accession AAW22593; and *Bos aurus* (Cattle): NCBI Accession XP_001250249.

The extracellular domain of TRAIL comprises amino acids 39-281, and the TNF domain responsible for receptor binding comprises amino acids 121-280, based on TNF homology models. The portion of the protein that is particularly important for conferring activity has been identified. See, e.g., Hymowitz et al., 1999, "Triggering cell death: The crystal structure of Apo2L/TRAIL in a complex with death receptor," *Am. Mol. Cell.* 4(4):563-71), incorporated herein by reference, which reports the most important amino acids for TRAIL binding to its receptor and activity comprise amino acids around the zinc area such as amino acids (191-201-205-207-236-237) and amino acids (150-216).

See also: (1) Krieg A et al., 2003, *Br. J of Cancer* 88: 918-927, which describes two human TRAIL variants without apoptotic activity, TRAIL-γ and TRAIL β; (2) Berg et al., 2007, "Enforced covalent trimerization increases the activity of the TNF ligand family members TRAIL and CD95L", *Cell death and differentiation* 14, 2021-2034; and (3) Cha et al., 2000, "Crystal Structure of TRAIL-DR5 complex identifies a critical role of the unique frame insertion in conferring recognition specificity," *J. Biol. Chem.* 275: 31171-31177 (2000), all incorporated herein by reference.

TRAIL is known to ligate two types of receptors: death receptors triggering TRAIL-induced apoptosis and decoy receptors that possibly inhibit this pathway. Four human receptors for TRAIL have been identified: TRAILR1, TRAILR2, TRAILR3 and TRAILR4. TRAILR1 and TRAILR2 when triggered induce apoptosis. However, TRAILR3 and TRAILR4 are decoy receptors that do not induce apoptosis. TRAIL can also bind to osteoprotegrin (OPG). Binding to each of these receptors has been well-characterized, e.g., Johnstone et al., "The TRAIL apoptotic pathway in cancer onset, progression and therapy," *Nature Reviews Cancer* Volume 8 (2008) 782-798.

The amino acid sequence of full-length human TRAIL (UniProtKG/Swiss-Prot accession number P50591.1) (SEQ ID NO:6) is shown below. The extracellular domain comprising amino acids 38-281 is underlined and in bold:

```
                                         (SEQ ID NO: 6)
MAMMEVQGGP SLGQTCVLIV IFTVLLQSLC VAVTYVYFTN

ELKQMQDKYS KSGIACFLKE DDSYWDPNDE ESMNSPCWQV

KWQLRQLVRK MILRTSEETI STVQEKQQNI SPLVRERGPQ

RVAAHITGTR GRSNTLSSPN SKNEKALGRK INSWESSRSG

HSFLSNLHLR NGELVIHEKG FYYIYSQTYF RFQEEIKENT

KNDKQMVQYI YKYTSYPDPI LLMKSARNSC WSKDAEYGLY

SIYQGGIFEL KENDRIFVSV TNEHLIDMDH EASFFGAFLV

G
```

In some preferred embodiments, Component B of the fusion protein comprises the following amino acid sequence (SEQ ID NO: 7) from human TRAIL:

```
                                         (SEQ ID NO: 7)
                    ETI STVQEKQQNI SPLVRERGPQ

RVAAHITGTR GRSNTLSSPN SKNEKALGRK INSWESSRSG

HSFLSNLHLR NGELVIHEKG FYYIYSQTYF RFQEEIKENT

KNDKQMVQYI YKYTSYPDPI LLMKSARNSC WSKDAEYGLY

SIYQGGIFEL KENDRIFVSV TNEHLIDMDH EASFFGAFLV

G
```

In some preferred embodiments, Component B of the fusion protein comprises the following amino acid sequence (SEQ ID NO:8) from human TRAIL:

(SEQ ID NO: 8)
RGPQ

RVAAHITGTR GRSNTLSSPN SKNEKALGRK INSWESSRSG

HSFLSNLHLR NGELVIHEKG FYYIYSQTYF RFQEEIKENT

KNDKQMVQYI YKYTSYPDPI LLMKSARNSC WSKDAEYGLY

SIYQGGIFEL KENDRIFVSV TNEHLIDMDH EASFFGAFLV

G

In some preferred embodiments, Component B of the fusion protein comprises the following amino acid sequence (SEQ ID NO: 9) from human TRAIL:

(SEQ ID NO: 9)
VRERGPQ RVAAHITGTR GRSNTLSSPN SKNEKALGRK

INSWESSRSG HSFLSNLHLR NGELVIHEKG FYYIYSQTYF

RFQEEIKENT KNDKQMVQYI YKYTSYPDPI LLMKSARNSC

WSKDAEYGLY SIYQGGIFEL KENDRIFVSV TNEHLIDMDH

EASFFGAFLV G.

In some embodiments, Component B of the fusion protein of the invention comprises the extracellular domain of the human TRAIL protein. In other embodiments, Component B of the fusion protein comprises a fragment of TRAIL comprising at least 20, 30, 40, 50, 60, 70, 80, 90, 100, 110, 120, 130, 140, 150, 160, 170, 180, 190, 200, 210, 220, 230, 240, 250, 260, 270 or 280 contiguous amino acids of the full-length TRAIL protein, wherein the fragment binds and triggers TRAIL receptor.

Component B: Fas Ligand

In another embodiment of the fusion protein of the invention, Component B comprises Fas ligand (FasL). FasL is a cytokine that binds to TNFRSF6/FAS, a receptor that transduces the apoptotic signal into cells. It may be involved in cytotoxic T-cell mediated apoptosis and in T-cell development. Fas-mediated apoptosis may have a role in the induction of peripheral tolerance, in the antigen-stimulated suicide of mature T cells, or both. Fas ligand has been sequenced in several species including human (UniProtKB/Swiss-Prot accession number P48023), mouse (GenBank accession number AAA19778. 1), horse (GenBank accession number ACV52391.1), cat (GenBank accession number BAC76426. 1) and cattle (GenBank accession number AEV59556.1).

The extracellular domain of Fas ligand comprises Fas ligand amino acids 103-281. The cytoplasmic domain comprises amino acids 1-80, and the transmembrane domain comprises amino acids 81-102.

The amino acid sequence of full-length human Fas ligand (FASLG; CD95L; FASL; TNFSF6) protein is shown below (SEQ ID NO: 10) (UniProtKB/Swiss-Prot accession number P48023). The extracellular domain, comprising amino acids 103-281, is underlined and in bold:

(SEQ ID NO: 10)
MQQPFNYPYP QIYWVDSSAS SPWAPPGTVL PCPTSVPRRP

GQRRPPPPPP PPPLPPPPPP PPLPPLPLPP LKKRGNHSTG

LCLLVMFFMV LVALVGLGLG MFQLFHLQKE LAELRESTSQ

MHTASSLEKQ IGHPSPPPEK KELRKVAHLT GKSNSRSMPL

EWEDTYGIVL LSGVKYKKGG LVINETGLYF VYSKVYFRGQ

SCNNLPLSHK VYMRNSKYPQ DLVMMEGKMM SYCTTGQMWA

RSSYLGAVFN LTSADHLYVN VSELSLVNFE ESQTFFGLYK

L

In some preferred embodiments, Component B of the fusion protein comprises the following amino acid sequence (SEQ ID NO: 11) from human FasL:

(SEQ ID NO: 11)
LEKQ IGHPSPPPEK KELRKVAHLT GKSNSRSMPL

EWEDTYGIVL LSGVKYKKGG LVINETGLYF VYSKVYFRGQ

SCNNLPLSHK VYMRNSKYPQ DLVMMEGKMM SYCTTGQMWA

RSSYLGAVFN LTSADHLYVN VSELSLVNFE ESQTFFGLYK

L

In some preferred embodiments, Component B of the fusion protein comprises the following amino acid sequence (SEQ ID NO: 12) from human FasL:

(SEQ ID NO: 12)
EKQ IGHPSPPPEK KELRKVAHLT GKSNSRSMPL

EWEDTYGIVL LSGVKYKKGG LVINETGLYF VYSKVYFRGQ

SCNNLPLSHK VYMRNSKYPQ DLVMMEGKMM SYCTTGQMWA

RSSYLGAVFN LTSADHLYVN VSELSLVNFE ESQTFFGLYK

L

In some embodiments, Component B of the fusion protein of the invention comprises the extracellular domain of the human FasL protein. In other embodiments, Component B of the fusion protein comprises a fragment of FasL protein comprising at least 20, 30, 40, 50, 60, 70, 80, 90, 100, 110, 120, 130, 140, 150, 160, 170, 180, 190, 200, 210, 220, 230, 240, 250, 260, 270 or 280 contiguous amino acids of the full-length FasL protein, wherein the fragment binds to and triggers Fas receptor.

Configuration of Fusion Protein

In the fusion protein of the present invention, when prepared by recombinant methods described elsewhere herein, the coding sequences of the two components are fused together in frame, either directly or through a linker. As used herein, the term "directly" refers to a fusion of the two components without a peptide linker in between (i.e., in an expression construct, the codons encoding Component A are contiguous with the codons encoding Component B). As used herein, "fused in frame" means that the expression of the fused coding sequences results in the fusion protein comprising both the first and the second polypeptides.

Accordingly, there is no translational terminator between the reading frames of the two components.

Components A and B need be in no particular order. In preferred embodiments, Component A is at the N-terminus of the protein, and Component B is at the C-terminus of the protein. In some embodiments, Component B is at the N-terminus of the protein, and Component A is at the C-terminus of the protein.

In one aspect of the invention, the N-terminus of Component B is fused to the C-terminus of Component A, either directly or indirectly via a peptide linker, resulting in NH₃-A-{optional linker}-B—COOH configuration. See FIG. 1A. In any of the embodiments, a linker peptide may optionally be present between Components A and B. In embodiments including an scFv, the variable domains may be arranged, N-terminal to C-terminal, either as $V_H$-$V_L$ or as $V_L$-$V_H$. In embodiments of the invention where the CD47 blocker is derived from a monoclonal antibody, the monoclonal antibody is preferably fully human. If not fully human, it is preferable that the framework sequence (between the CDRs of the variable regions) be human, e.g., a humanized antibody. Where the agonist is a $V_H C_H$, it is preferred that at least the $C_H$ domain is human, e.g., a chimeric antibody. The $V_H$ domain of the $V_H C_H$ may also be humanized.

In one aspect, the fusion protein comprises CD blocker derived from a monoclonal anti-CD47 antibody fused to TRAIL, or functional fragment thereof, or FasL or functional fragment thereof. In some embodiments, the CD blocker is selected from the group consisting of scFvCD47, $V_H C_H$CD47, and $V_H$HCD47.

In one embodiment, the fusion protein comprises scFvCD47 fused to TRAIL or FasL. See FIG. 1B. In one embodiment, the scFvCD47 comprises the $V_H$ and $V_L$ chains of a monoclonal antibody against human CD47 and Component B is a fragment of TRAIL comprising or consisting of: SEQ ID NO:9.

In one embodiment, the scFvCD47 comprises the $V_H$ and $V_L$ chains of a monoclonal antibody against human CD47 and Component B is a fragment of Fas L comprising or consisting of SEQ ID NO: 12.

In another embodiment, the fusion protein comprises $V_H C_H$CD47 fused to TRAIL, or functional fragment thereof, or FasL, or functional fragment thereof. See FIG. 1C. In one embodiment, $V_H C_H$CD47 comprises the $V_H$ and constant region of the heavy chain of a monoclonal antibody against human CD47 and Component B comprises or consists of SEQ ID NO: 9 or SEQ ID NO: 12.

The embodiments including an antibody derivative as Component A typically include a linker between Components A and B to enable proper folding of the two components and minimize steric problems.

In another aspect, the fusion protein comprises the ectodomain of SIRP alpha as Component A. In an embodiment, the fusion protein comprises the ectodomain of SIRP alpha, or functional fragment thereof, as Component A, fused directly or indirectly via a peptide linker to TRAIL, or a functional fragment thereof, or Fas L, or a functional fragment thereof, as Component B. See FIG. 1D. In one embodiment, the SIRP alpha is from human SIRP alpha and Component B is human TRAIL or human Fas L, or functional fragment thereof. In an embodiment, Component A comprises or consists of SEQ ID NO: 1, and Component B is a functional fragment of TRAIL comprising or consisting of SEQ ID NO: 9.

In a preferred embodiment, the fusion protein of the invention comprises or consists of the sequence:

```
                                            (SEQ ID NO: 13)
GVAGEEELQVIQPDKSVLVAAGETATLRCTATSLIPVGPIQWFRGAGP

GRELIYNQKEGHFPRVTTVSDLTKRNNMDFSIRIGNITPADAGTYYCV

KFRKGSPDDVEFKSGAGTELSVRAKPSAPVVSGPAARATPQHTVSFTC

ESHGFSPRDITLKWFKNGNELSDFQTNVDPVGESVSYSIHSTAKVVLT

REDVHSQVICEVAHVTLQGDPLRGTANLSETIRVPPTLEVTQQPVRAE

NQVNVTCQVRKFYPQRLQLTWLENGNVSRTETASTVTENKDGTYNWMS

WLLVNVSAHRDDVKLTCQVEHDGQPAVSKSHDLKVSAHPKEQGSNTAA

ENTGSNERNIYGDPLVTAASVLEFGGSGGGSEGGGSEGGGSEGGGSDI

VRERGPQRVAAHITGTRGRSNTLSSPNSKNEKALGRKINSWESSRSGH

SFLSNLHLRNGELVIHEKGFYYIYSQTYFRFQEEIKENTKNDKQMVQY

IYKYTSYPDPILLMKSARNSCWSKDAEYGLYSIYQGGIFELKENDRIF

VSVTNEHLIDMDHEASFFGAFLVG.
```

In another preferred embodiment, the fusion protein of the invention comprises or consists of the sequence:

```
                                            (SEQ ID NO: 14)
ASHHHHHHMGVAGEEELQVIQPDKSVLVAAGETATLRCTATSLIPVGP

IQWFRGAGPGRELIYNQKEGHFPRVTTVSDLTKRNNMDFSIRIGNITP

ADAGTYYCVKFRKGSPDDVEFKSGAGTELSVRAKPSAPVVSGPAARAT

PQHTVSFTCESHGFSPRDITLKWFKNGNELSDFQTNVDPVGESVSYSI

HSTAKVVLTREDVHSQVICEVAHVTLQGDPLRGTANLSETIRVPPTLE

VTQQPVRAENQVNVTCQVRKFYPQRLQLTWLENGNVSRTETASTVTEN

KDGTYNWMSWLLVNVSAHRDDVKLTCQVEHDGQPAVSKSHDLKVSAHP

KEQGSNTAAENTGSNERNIYGDPLVTAASVLEFGGSGGGSEGGGSEGG

GSEGGGSDIVRERGPQRVAAHITGTRGRSNTLSSPNSKNEKALGRKIN

SWESSRSGHSFLSNLHLRNGELVIHEKGFYYIYSQTYFRFQEEIKENT

KNDKQMVQYIYKYTSYPDPILLMKSARNSCWSKDAEYGLYSIYQGGIF

ELKENDRIFVSVTNEHLIDMDHEASFFGAFLVG.
```

In another aspect, the fusion protein comprises the ectodomain of SIRP gamma or TSP CBD as Component A. In an embodiment, the fusion protein comprises the ectodomain of SIRP gamma or functional fragment thereof, as Component A, fused directly or indirectly via a peptide linker to TRAIL, or a functional fragment thereof, or Fas L, or a functional fragment thereof, as Component B. See FIG. 1E.

In an embodiment, the fusion protein comprises TSP CBD or functional fragment thereof, as Component A, fused directly or indirectly via a peptide linker to TRAIL or a functional fragment thereof, or Fas L or a functional fragment thereof, as Component B. See FIG. 1F.

Linkers

In some embodiments, the components of the fusion protein of the invention may be optionally connected via a peptide linker. The residues for the linker may be selected from naturally occurring amino acids, non-naturally occurring amino acids, and modified amino acids. The linker will typically connect the carboxy terminus of the first component to the amino terminus of the second component. The linker may alter the distance between the two structural components of the fusion protein, as well as alter the flexibility of this region. The linker may comprise any number of amino acids. The linker may thus comprise, for example, 1, 2, 3, 4, 5, 6, 7, 8, 9, 10, 11, 12, 13, 14, 15, 16, 17, 18, 19, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, or more amino acids. In some embodiments, the linker may be composed of from 3 to 60 amino acid residues, from 3 to 40 amino acids, from 3 to 30 amino acids, from 3 to 24 amino acids, from 3 to 18 amino acids, or from 3 to 15 amino acids. The linker may comprise, for example, a repeating sub-sequence of 2, 3, 4, 5 or more amino acid residues, comprising 2, 3, 4, 5, 6, 7, 8, 9, 10, 11, 12 or more repeats of the sub-sequence.

Linkers may be naturally-occurring sequences or designed sequences. Peptide linkers useful in the molecule of the invention include, but are not limited to, glycine linkers, glycine-rich linkers, serine-glycine linkers, and the like. A glycine-rich linker comprises at least about 50% glycine and preferably at least about 60% glycine. In one embodiment, the linker comprises the amino acid sequence Gly-Ser, or repeats thereof. See, e.g., Huston, et al., *Methods in Enzymology*, 203:46-88 (1991). In another embodiment, the linker comprises the amino acid sequence Glu-Lys, or repeats thereof. See, e.g., Whitlow et al., *Protein Eng.*, 6:989 (1993)). In another embodiment, the linker comprises the amino acid sequence Gly-Gly-Ser, or repeats thereof. In another embodiment, the linker comprises the amino acid sequence Gly-Gly-Gly-Gly-Ser (SEQ ID NO: 15), or repeats thereof. In certain specific embodiments, the linker contains from 2 to 12 repeats of Gly-Gly-Ser or Gly-Gly-Gly-Gly-Ser (SEQ ID NO:16). See U.S. Pat. No. 6,541,219 for examples of peptide linkers. In one embodiment, the linker may comprise the sequence:

```
                                    (SEQ ID NO: 17)
GDPLVTAASVLEFGGSGGGSEGGGSEGGGSEGGGSDI.
```

Linkers comprising human immunoglobulin Fc region sequences are also useful. An exemplary Fc region linker includes but is not limited to: the hinge region of human IgG1 (EPKSCDKTHTCPPCP; SEQ ID NO: 18); the $C_{H2}$ and $C_{H3}$ domains of aglycosyl human IgG1; and a second IgG1 hinge region. An exemplary sequence for this linker comprises the following sequence, wherein the hinge region sequences are underlined:

```
                                    (SEQ ID NO: 19)
EPKSCDKTHT CPPCPAPELL GGPSVFLFPP KPKDTLMISR

TPEVTCVVVD VSHEDPEVKF NWYVDGVEVH NAKTKPREEQ

YNSTYRVVSV LTVLHQDWLN GKEYKCKVSN KALPAPIEKT

ISKAKGQPRE PQVYTLPPSR DELTKNQVSL TCLVKGFYPS

DIAVEWESNG QPENNYKTTP PVLDSDGSFF LYSKLTVDKS

RWQQGNVFSC SVMHEALHNH YTQKSLSLSP GKEPKSCDKT

HTCPPCP.
```

In another embodiment, the hinge region and the $C_{H2}$ and $C_{H3}$ domains of human IgG1 are mutated to prevent inter-chain disulfide bonds, to reduce antibody dependent cellular cytotoxicity (ADCC), or to eliminate N-linked glycosylation (aglycosyl human IgG1). An exemplary sequence for this linker comprises the sequence below, wherein mutated sequences are in bold and underlined.

```
                                    (SEQ ID NO: 20)
EPKSSDKTHT SPPSPAPPVA GAPSVFLFPP KPKDTLMISR

TPEVTCVVVD VSHEDPEVKF NWYVDGVEVH NAKTKPREEQ

YASTYRVVSV LTVLHQDWLN GKEYKCKVSN KALPAPIEKT

ISKAKGQPRE PQVYTLPPSR DELTKNQVSL TCLVKGFYPS

DIAVEWESNG QPENNYKTTP PVLDSDGSFF LYSKLTVDKS

RWQQGNVFSC SVMHEALHNH YTQKSLSLSP GK.
```

Linkers are useful for separating the two components of the fusion protein to enable proper folding of the components, to reduce potential steric problems, and/or to contribute optimal receptor binding. The skilled artisan is familiar with the design and selection of peptide linkers. See, for instance, Robinson et al., 1998, *Proc. Natl. Acad. Sci. USA* 95:5929-5934. Automated programs are also available for peptide linker design (e.g., Crasto et al., 2000, *Protein Engineering* 13:309-312).

Optional Other Elements

The fusion protein optionally may also include further elements apart from Component A, Component B and the optional linker. Such further elements may include: an initiator methionine, a signal peptide, an antigen polypeptide, a trimerization domain, and a purification tag, such as His-6. An exemplary purification tag is ASHHHHHHM (SEQ ID NO: 21). In an embodiment, the fusion protein of the invention consists essentially of a purification tag, Component A and Component B, and an optional linker and an optional trimerization domain. In some embodiments, fusion proteins essentially consisting of Component A and Component B and an optional linker are preferred.

Fusion proteins of the invention optionally comprise a signal peptide. Signal peptides can be varied according to the needs of the user, the expression system, and other factors, as would be understood by one skilled in the art. Signal peptides are well known in the art, and any desired signal peptide can be used, including those recognized/predicted by publicly available signal peptide recognition software known to those skilled in the art.

TRAIL and FasL both require trimerization for optimal receptor binding. Naturally-occurring TRAIL and FasL each can form trimers, however, the trimers can be unstable. Thus, addition of a heterologous trimerization domain to TRAIL and FasL may further increase receptor binding affinity by increasing the likelihood of formation and stabilization of the resulting protein. Thus, in an embodiment, the fusion protein of the invention optionally further comprises a heterologous trimerization domain. Within the fusion protein, the heterologous trimerization domain may be positioned anywhere within the fusion protein, provided it does not disrupt the functional activity of the fusion protein, e.g., binding to and blocking SIRP alpha triggering on phagocytotic cells. Similarly, the heterologous trimerization domain should not disrupt the binding and triggering function of the TRAIL or FasL domain. The heterologous trimerization domain may be positioned within Component A, or between Component A and the optional linker, or within or in place of the optional linker, or between the optional linker and Component B, or at the C-terminal terminus of the fusion protein. It is preferable that the heterologous trimerization domain is positioned substantially adjacent to Component B, to optimize the formation of Component B trimers. In a preferred embodiment, however, the trimerization domain is not positioned at the C-terminal terminus of the fusion protein.

Trimerization domains are well known in the art. Non-limiting examples of trimerization domains suitable as a heterologous trimerization domain in the fusion protein of the invention include: the GCN4 leucine zipper (Harbury et al., 1993, "A switch between two-, three-, and four-stranded coiled coils in GCN4 leucine zipper mutants," *Science* 262(5138):1401-7); a 35 amino-acid sequence from lung surfactant protein (Hoppe et al., 1994, "A parallel three stranded alpha-helical bundle at the nucleation site of collagen triple-helix formation," *FEBSLett.* 344(2-3): 191-5); short, repeating heptad sequences from collagen (McAlinden et al., 2003, "Alpha-helical coiled-coil oligomerization domains are almost ubiquitous in the collagen superfamily," *J Biol Chem.* 278(43):42200-7. Epub 2003 August 14.); and the bacteriophage T4 fibritin "foldon" (see, e.g., Miroshnikov et al., 1998, "Engineering trimeric fibrous proteins based on bacteriophage T4 adhesins," *Protein Eng.* 11(4): 329-32). Exemplary trimerization domains are also disclosed in U.S. Pat. Nos. 6,911,205 and 8,147,843, and U.S. Pat. Appln. Pub. 2010/0136032. An exemplary trimerization sequence is the T4 "foldon" having the sequence: GYIPEAPRDGQAYVRKRGEWVLLSTFL (SEQ ID NO: 22). Another exemplary trimerization domain is from thrombospondin-1 and has the sequence:

```
                    (SEQ ID NO: 23)
VTTLQDSIRKVTEENKELANELRR.
```

Modification

This invention relates to a fusion protein comprising a CD47 blocker and TRAIL, or functional fragment thereof, or Fas L, or functional fragment thereof. The invention also encompasses variants of the fusion proteins. While in general it is desirable for variants to show enhanced ability for binding to a given molecule, in some embodiments variants may be designed with slightly reduced activity as compared to other fusion proteins of the invention, for example, in instances in which one would purposefully want to attenuate activity. Furthermore, variants or derivatives can be generated that would have altered multimerization properties. When engineering variants, for instance, of the ectodomain of SIRP alpha, this could be done for either the entire SIRP alpha soluble ectodomain, or for that component of the ectodomain that is incorporated within the fusion protein itself. Moreover, variants or derivatives can be generated that would bind more selectively to one of the TRAIL receptor variants (there are two TRAIL receptors in humans that induce apoptosis). Similarly, variants or derivatives of TRAIL can be generated that would have altered multimerization properties. When engineering variants, this could be done for either the entire TRAIL extracellular domain, or for that component of the extracellular domain that is incorporated within the fusion protein itself.

Preferably, variants or derivatives of the fusion proteins of the present invention maintain the hydrophobicity/hydrophilicity of the amino acid sequence.

In additional embodiments, the fusion protein of the invention is a variant and/or derivative of the amino acid sequence shown in SEQ. ID. NOs. 13 or 14. In one embodiment, variants of the fusion proteins of the present invention will have at least 80% or greater sequence identity or homology, as those terms are understood in the art, to SEQ ID NO: 13 or SEQ ID NO: 14, more preferably at least 85%, 86%, 87%, 88%, 89%, 90%, 91%, 92%, 93%, 94%, 95%, 96%, 97%, 98%, or even 99% sequence identity to SEQ ID NO: 13 or SEQ ID NO: 14.

The invention also provides chemical modification of a fusion protein of the invention. Non-limiting examples of such modifications may include but are not limited to aliphatic esters or amides of the carboxyl terminus or of residues containing carboxyl side chains, O-acyl derivatives of hydroxyl group-containing residues, and N-acyl derivatives of the amino-terminal amino acid or amino-group containing residues, e.g., lysine or arginine.

Additional modifications can include, for example, production of a fusion protein conjugated with polyethylene glycol (PEG), or addition of PEG during chemical synthesis of a polypeptide of the invention. Modifications of polypeptides or portions thereof can also include reduction/alkylation; chemical coupling to an appropriate carrier or mild formalin treatment.

Other derivatives of the fusion proteins of the present invention include incorporation of unnatural amino acid residues, or phosphorylated amino acid residues such as phosphotyrosine, phosphoserine or phosphothreonine residues. Other potential modifications include sulfonation, biotinylation, or the addition of other moieties, particularly those which have molecular shapes similar to phosphate groups.

Derivatives also include polypeptides modified by glycosylation. These can be made by modifying glycosylation patterns during synthesis and processing in various alternative eukaryotic host expression systems, or during further processing steps. Methods for producing glycosylation modifications include exposing the fusion proteins to glycosylating enzymes derived from cells that normally carry out such processing, such as mammalian glycosylation enzymes. Alternatively, deglycosylation enzymes can be used to remove carbohydrates attached during production in eukaryotic expression systems. Additionally, one can also modify the coding sequence so that glycosylation site(s) are added or glycosylation sites are deleted or disabled. Furthermore, if no glycosylation is desired, the proteins can be produced in a prokaryotic host expression system.

Variants and/or derivatives of the fusion proteins of the invention can be prepared by chemical synthesis or by using site-directed mutagenesis (Gillman et al., *Gene* 8:81 (1979); Roberts et al., *Nature* 328:731 (1987) or Innis (Ed.), 1990, *PCR Protocols: A Guide to Methods and Applications, Academic Press*, New York, N.Y.) or the polymerase chain reaction method (PCR; Saiki et al., *Science* 239:487 (1988)), as exemplified by Daugherty et al., *Nucleic Acids Res.* 19:2471 (1991)) to modify nucleic acids encoding the complete receptors.

Additional modifications can be introduced such as those that further stabilize the TRAIL trimer and/or increase affinity of binding to TRAIL receptor, or stabilize the Fas L trimer and/or increase affinity of binding to Fas receptor. As discussed elsewhere herein, spacers/linkers can be added to alter the distance between the two structural components of the fusion protein, as well as alter the flexibility of this region.

In additional embodiments, the fusion proteins of the present invention may further comprise one or more additional polypeptide domains added to facilitate protein purification, to increase expression of the recombinant protein, or to increase the solubility of the recombinant protein. Such purification/expression/solubility facilitating domains include, but are not limited to, metal chelating peptides such as histidine-tryptophan modules that allow purification on immobilized metals (Porath, 1992, *Protein Expr Purif* 3-0.26328 1), protein A domains that allow purification on immobilized immunoglobulin, and the domain utilized in the FLAGS extension/affinity purification system (Immunex Corp, Seattle, Wash.). The inclusion of a cleavable linker sequence such as Factor Xa or enterokinase (Invitrogen, San Diego, Calif.) between the purification domain and the fusion of Components A and B is useful to facilitate purification.

Fusion expression vectors include pGEX (Pharmacia, Piscataway, N.J.), pMAL (New England Biolabs, Beverly, Mass.) and pRITS (Pharmacia, Piscataway, N.J.) which fuse glutathione S transferase (GST), maltose B binding protein, or protein A, respectively, to the target recombinant protein. EBV, BKV, and other episomal expression vectors (Invitrogen) can also be used. In addition, retroviral and lentiviral expression vectors can also be used. Furthermore, any one of a number of in vivo expression systems designed for high level expression of recombinant proteins within organisms can be invoked for producing the fusion proteins specified herein.

As discussed above, a fusion protein of the present invention may contain a heterologous signal sequence at its N-terminus. In certain host cells (e.g., mammalian host cells), expression and/or secretion of the fusion protein can be increased through use of a heterologous signal sequence. Signal sequences are typically characterized by a core of hydrophobic amino acids, which are generally cleaved from the mature protein during secretion in one or more cleavage events. Such signal peptides contain processing sites that allow cleavage of the signal sequence from the mature proteins as they pass through the secretory pathway. Thus, the invention pertains to the described polypeptides having a signal sequence, as well as to polypeptides from which the signal sequence has been proteolytically cleaved (i.e., the cleavage products).

In order to enhance stability and/or reactivity, the fusion protein of the present invention can also be modified to incorporate one or more polymorphisms in the amino acid sequence resulting from natural allelic variation. Additionally, D-amino acids, non-natural amino acids or non-amino acid analogues can be substituted or added to produce a modified fusion protein within the scope of this invention.

The amino acid sequences of the present invention may be produced by expression of a nucleotide sequence coding for same in a suitable expression system.

In addition, or in the alternative, the fusion protein itself can be produced using chemical methods to synthesize the desired amino acid sequence, in whole or in part. For example, polypeptides can be synthesized by solid phase techniques, cleaved from the resin, and purified by preparative high performance liquid chromatography (e.g., Creighton (1983) *Proteins: Structures And Molecular Principles*, WH Freeman and Co, New York N.Y.). The composition of the synthetic polypeptides may be confirmed by amino acid analysis or sequencing (e.g., the Edman degradation procedure). Additionally, the amino acid sequence of a fusion protein of the invention, or any part thereof, may be altered during direct synthesis and/or combined using chemical methods with a sequence from other subunits, or any part thereof, to produce a variant polypeptide.

Assays for measuring the biological activity of any homolog, derivative or variant of any fusion protein of the present invention are well known in the art.

For example, any one of several conventional assays for monitoring inhibition of SIRP alpha activation in macrophages can be invoked.

Activity and Utility

In one embodiment, the fusion proteins of the present invention reduce or prevent a tumor cell from evading phagocytosis by a phagocytic cell, such as a macrophage, while also promoting apoptosis of the tumor cell. In other embodiments, the fusion proteins of the invention reduce or prevent a tumor cell from evading phagocytosis by a phagocytic cell, while promoting apoptosis of a neighboring tumor cell expressing an activated TRAIL receptor or Fas. Thus, the fusion proteins of the present invention promote tumor cell death.

The fusion protein of the invention advantageously provides dual-signaling capability within a single cell expressing both CD47 and an activated TRAIL receptor or Fas L receptor. The dual-signaling capacity is also efficacious in bridging CD47-expressing cells and TRAIL receptor or Fas L receptor-expressing cells. The dual-signaling capacity thus offers increased efficacy over, for instance, CD47 blocking alone as with scFvCD47:Fc fusion protein. In addition, the fusion protein of the invention offers increased signaling from co-localization (clustering) of receptors. The fusion protein of the invention also provided enhanced specificity for cells expressing both CD47 and TRAIL receptors or Fas L receptors, and functional synergies may be achieved.

Functional synergy may also arise from higher order oligomer forms of the fusion protein of the invention. Recent evidence indicates that extracellular domains of SIRP alpha spontaneously form dimers and oligomers in solution and on the cell surface, however, SIRP alpha dimerization is not necessary for binding to CD47 (Lee et al., 2010, "The role of cis dimerization of signal regulatory protein alpha (SIRPalpha) in binding to CD47," *J Biol Chem.* 285(49):37953-63). Both TRAIL and Fas L form trimers. Thus, a hexamer of the fusion protein of the invention, which is comprised of a "trimer of dimers" on one end (Component A) and a "dimer of trimers on the other end (Component B) is possible. This higher order oligomer form is expected to markedly enhance the functionality of the fusion protein, especially with respect to Fas L signaling. The invention is not, however, limited to such an oligomeric form.

Enhanced specificity may lead to lower doses for achieving comparable efficacy relative to prior art individual receptor triggering fusion proteins, such as CD47-Fc. It is also contemplated that the enhanced specificity may lead to reduced dosing frequency needed for achieving comparable efficacy, relative to prior art individual receptor triggering fusion proteins. Reduction in dosing and/or dosing frequency advantageously may reduce undesirable side effects that can arise in individual receptor triggering fusions, such as CD47:Fc.

The fusion protein of the invention has therapeutic utility in any disease characterized by expression of CD47 and an activated TRAIL receptor or an activated Fas L receptor.

CD47 is expressed on a wide range of tumor cells, such a solid tumor cells. Thus, in one embodiment, the invention provides a method of treating a proliferative disorder by administering a therapeutically effective amount of a fusion protein of the invention to a subject diagnosed with a proliferative disorder.

The fusion proteins according to the invention may be administered to individuals (such as mammals, including animals and humans) afflicted with a cellular proliferative disorder such as cancer, and malignant and benign tumors. In a particular embodiment of the invention, the individual treated is a human.

The fusion proteins are believed effective against a broad range of tumor types, including but not limited to the following: ovarian cancer; cervical cancer; breast cancer; prostate cancer; testicular cancer, lung cancer, renal cancer; colorectal cancer; skin cancer; brain cancer; leukemia, including acute myeloid leukemia, chronic myeloid leukemia, acute lymphoid leukemia, and chronic lymphoid leukemia.

More particularly, cancers that may be treated by the compounds, compositions and methods of the invention include, but are not limited to, the following:

cardiac cancers, including, for example sarcoma, e.g., angiosarcoma, fibrosarcoma, rhabdomyosarcoma, and liposarcoma; myxoma; rhabdomyoma; fibroma; lipoma and teratoma;

lung cancers, including, for example, bronchogenic carcinoma, e.g., squamous cell, undifferentiated small cell, undifferentiated large cell, and adenocarcinoma; alveolar and bronchiolar carcinoma; bronchial adenoma; sarcoma; lymphoma; chondromatous hamartoma; and mesothelioma;

gastrointestinal cancer, including, for example, cancers of the esophagus, e.g., squamous cell carcinoma, adenocarcinoma, leiomyosarcoma, and lymphoma; cancers of the stomach, e.g., carcinoma, lymphoma, and leiomyosarcoma; cancers of the pancreas, e.g., ductal adenocarcinoma, insulinoma, glucagonoma, gastrinoma, carcinoid tumors, and vipoma; cancers of the small bowel, e.g., adenocarcinoma, lymphoma, carcinoid tumors, Kaposi's sarcoma, leiomyoma, hemangioma, lipoma, neurofibroma, and fibroma; cancers of the large bowel, e.g., adenocarcinoma, tubular adenoma, villous adenoma, hamartoma, and leiomyoma;

genitourinary tract cancers, including, for example, cancers of the kidney, e.g., adenocarcinoma, Wilm's tumor (nephroblastoma), lymphoma, and leukemia; cancers of the bladder and urethra, e.g., squamous cell carcinoma, transitional cell carcinoma, and adenocarcinoma; cancers of the prostate, e.g., adenocarcinoma, and sarcoma; cancer of the testis, e.g., seminoma, teratoma, embryonal carcinoma, teratocarcinoma, choriocarcinoma, sarcoma, interstitial cell carcinoma, fibroma, fibroadenoma, adenomatoid tumors, and lipoma;

liver cancers, including, for example, hepatoma, e.g., hepatocellular carcinoma; cholangiocarcinoma; hepatoblastoma; angiosarcoma; hepatocellular adenoma; and hemangioma;

bone cancers, including, for example, osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochrondroma (osteocartilaginous exostoses), benign chondroma, chondroblastoma, chondromyxofibroma, osteoid osteoma and giant cell tumors;

nervous system cancers, including, for example, cancers of the skull, e.g., osteoma, hemangioma, granuloma, xanthoma, and osteitis deformans; cancers of the meninges, e.g., meningioma, meningiosarcoma, and gliomatosis; cancers of the brain, e.g., astrocytoma, medulloblastoma, glioma, ependymoma, germinoma (pinealoma), glioblastoma multiform, oligodendroglioma, schwannoma, retinoblastoma, and congenital tumors; and cancers of the spinal cord, e.g., neurofibroma, meningioma, glioma, and sarcoma;

gynecological cancers, including, for example, cancers of the uterus, e.g., endometrial carcinoma; cancers of the cervix, e.g., cervical carcinoma, and pre-tumor cervical dysplasia; cancers of the ovaries, e.g., ovarian carcinoma, including serous cystadenocarcinoma, mucinous cystadenocarcinoma, unclassified carcinoma, granulosa-thecal cell tumors, Sertoli-Leydig cell tumors, dysgerminoma, and malignant teratoma; cancers of the vulva, e.g., squamous cell carcinoma, intraepithelial carcinoma, adenocarcinoma, fibrosarcoma, and melanoma; cancers of the vagina, e.g., clear cell carcinoma, squamous cell carcinoma, botryoid sarcoma, and embryonal rhabdomyosarcoma; and cancers of the fallopian tubes, e.g., carcinoma;

hematologic cancers, including, for example, cancers of the blood, e.g., acute myeloid leukemia, chronic myeloid leukemia, acute lymphoblastic leukemia, chronic lymphocytic leukemia, myeloproliferative diseases, multiple myeloma, and myelodysplastic syndrome, Hodgkin's lymphoma, non-Hodgkin's lymphoma (malignant lymphoma) and Waldenström's macroglobulinemia, angioimmunoblastic T-cell lymphoma (AITL), chronic lymphocytic leukemia (CLL), acute nonlymphocytic leukemia, chronic lymphocytic leukemia, acute granulocytic leukemia, chronic granulocytic leukemia, monocytic leukemia, myeloblastic leukemia, myelocytic leukemia, myeloid granulocytic leukemia, myelomonocytic leukemia, Naegeli leukemia, plasma cell leukemia, plasmacytic leukemia, promyelocytic leukemia, Rieder cell leukemia, Schilling's leukemia, stem cell leukemia, subleukemic leukemia, acute promyelocytic leukemia, adult T-cell leukemia, aleukemic leukemia, aleukocythemic leukemia, basophilic leukemia, blast cell leukemia, bovine leukemia, chronic myelocytic leukemia, leukemia cutis, embryonal leukemia, undifferentiated cell leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia and micromyeloblastic leukemia;

skin cancers, including, for example, malignant melanoma, basal cell carcinoma, squamous cell carcinoma, Kaposi's sarcoma, moles dysplastic nevi, lipoma, angioma, dermatofibroma, keloids, psoriasis; and adrenal gland cancers, including, for example, neuroblastoma.

More particular examples of such cancers include kidney or renal cancer, breast cancer, colon cancer, rectal cancer, colorectal cancer, lung cancer including small-cell lung cancer, non-small cell lung cancer, adenocarcinoma of the lung and squamous carcinoma of the lung, squamous cell cancer (e.g. epithelial squamous cell cancer), cervical cancer, ovarian cancer, prostate cancer, liver cancer, bladder cancer, cancer of the peritoneum, hepatocellular cancer, gastric or stomach cancer including gastrointestinal cancer, gastrointestinal stromal tumors (GIST), pancreatic cancer, head and neck cancer, glioblastoma, retinoblastoma, astrocytoma, thecomas, arrhenoblastomas, hepatoma, hematologic malignancies including non-Hodgkins lymphoma (NHL), multiple myeloma and acute hematologic malignancies, endometrial or uterine carcinoma, endometriosis, fibrosarcomas, choriocarcinoma, salivary gland carcinoma, vulval cancer, thyroid cancer, esophageal carcinomas, hepatic carcinoma, anal carcinoma, penile carcinoma, nasopharyngeal carcinoma, laryngeal carcinomas, Kaposi's sarcoma, melanoma, skin carcinomas, Schwannoma, oligodendroglioma, neuroblastomas, rhabdomyosarcoma, osteogenic sarcoma, leiomyosarcomas, urinary tract carcinomas, thyroid carcinomas, Wilm's tumor, as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia); chronic lymphocytic leukemia (CLL); acute lymphoblastic leukemia (ALL); acute myelogenous leukemia (AML); Hairy cell leukemia; chronic myeloblastic leukemia; and post-transplant lymphoproliferative disorder (PTLD), as well as abnormal vascular proliferation associated with phakomatoses, edema (such as that associated with brain tumors), and Meigs' syndrome. "Tumor", as used herein, refers to all neoplastic cell growth and proliferation, whether malignant or benign, and all pre-cancerous and cancerous cells and tissues Cancers may be solid tumors that may or may not be metastatic. Cancers may also occur, as in leukemia, as a diffuse tissue. Thus, the term "tumor cell", as provided herein, includes a cell afflicted by any one of the above identified disorders.

In a preferred embodiment, the cancer is a solid tumor. In preferred embodiments, the cancer is one of pancreatic cancer, breast cancer, ovarian cancer, bladder cancer, melanoma and glioblastoma.

In another embodiment, the cancer is a hematologic cancer. In preferred embodiments, the hematological cancer is one of acute lymphoblastic leukemia (ALL) and acute myelogenous leukemia (AML).

CD47 is also broadly expressed on non-cancerous cells. In some non-cancerous proliferative disorders, the cells express both CD47 and an activated TRAIL receptor or an activated Fas L receptor. Thus, the fusion protein of the invention has therapeutic utility for such non-cancerous proliferative disorders. Examples of non-cancerous cellular proliferative disorders include those in which there is aberrant fibrogenesis due to accumulation and proliferation of myofibroblasts. Myofibroblasts are the cells that are responsible for the production of fibrous tissue in pathogenic contexts. For example, the pancreatic fibrosis associated with chronic pancreatitis has been linked to conversion of fibroblastic stellate cells in the pancreas to myofibroblasts. These stellate cells are known to bear TRAIL and Fas receptors. Accordingly, the fusion protein of the present invention could be used to eliminate the stellate cells and the generation of pathogenic myofibroblasts. Additionally, myofibroblasts are thought to be associated with aberrant fibrogenesis in various other disease settings. The fusion protein of the invention would also be expected to be relevant to them as well.

Pharmaceutical Compositions and Dosing Regimens.

Administration of the compositions of the invention is typically parenteral, by subcutaneous, intravenous, intramuscular, or intraperitoneal injection, or by infusion or by any other acceptable systemic method. In a preferred embodiment, administration is by subcutaneous injection. In another preferred embodiment, administration is by intravenous infusion, which may typically take place over a time course of about 1 to 5 hours. In addition, there are a variety of oral delivery methods for administration of therapeutic proteins, and these can be applied to the therapeutic fusion proteins of this invention.

Often, treatment dosages are titrated upward from a low level to optimize safety and efficacy. Generally, daily dosages will fall within a range of about 0.01 to 20 mg protein per kilogram of body weight. Typically, the dosage range will be from about 0.1 to 5 mg protein per kilogram of body weight. Various modifications or derivatives of the fusion proteins, such as addition of polyethylene glycol chains (PEGylation), may be made to influence their pharmacokinetic and/or pharmacodynamic properties.

To administer the fusion protein by other than parenteral administration, it may be necessary to coat the protein with, or co-administer the protein with, a material to prevent its inactivation. For example, protein may be administered in an incomplete adjuvant, co-administered with enzyme inhibitors or in liposomes. Enzyme inhibitors include pancreatic trypsin inhibitor, diisopropylfluorophosphate (DEP) and trasylol. Liposomes include water-in-oil-in-water CGF emulsions as well as conventional liposomes (Strejan et al., 1984, *J. Neuroimmunol.* 7:27).

Although the compositions of the invention can be administered in simple solution, they are more typically used in combination with other materials such as carriers, preferably pharmaceutically acceptable carriers. Useful pharmaceutically acceptable carriers can be any compatible, non-toxic substance suitable for delivering the compositions of the invention to a patient. Sterile water, alcohol, fats, waxes, and inert solids may be included in a carrier. Pharmaceutically acceptable adjuvants (buffering agents, dispersing agents) may also be incorporated into the pharmaceutical composition. Generally, compositions useful for parenteral administration of such drugs are well known; e.g., *Remington's Pharmaceutical Science*, 17th Ed. (Mack Publishing Company, Easton, Pa., 1990). Alternatively, compositions of the invention may be introduced into a patient's body by implantable drug delivery systems (Urquhart et al., 1984, *Ann. Rev. Pharmacol. Toxicol.* 24:199).

Therapeutic formulations may be administered in many conventional dosage formulations. Formulations typically comprise at least one active ingredient, together with one or more pharmaceutically acceptable carriers. Formulations may include those suitable for oral, rectal, nasal, or parenteral (including subcutaneous, intramuscular, intravenous and intradermal) administration.

The formulations may conveniently be presented in unit dosage form and may be prepared by any methods well known in the art of pharmacy. See, e.g., Gilman et al. (eds.) (1990), *The Pharmacological Bases of Therapeutics*, 8th Ed., Pergamon Press; and *Remington's Pharmaceutical Sciences*, supra, Easton, Pa.; Avis et al. (eds.) (1993) *Pharmaceutical Dosage Forms: Parenteral Medications*, Dekker, N.Y.; Lieberman et al. (eds.) (1990) *Pharmaceutical Dosage Forms: Tablets*, Dekker, N.Y.; and Lieberman et al. (eds.) (1990), *Pharmaceutical Dosage Forms: Disperse Systems*, Dekker, N.Y.

In additional embodiments, the present invention contemplates administration of the fusion proteins by gene therapy methods, e.g., administration of an isolated nucleic acid encoding a fusion protein of interest. The protein building blocks (e.g., Component A and Component B) of the fusion protein of the present invention have been well-characterized, both as to the nucleic acid sequences encoding the proteins and the resultant amino acid sequences of the proteins. Engineering of such isolated nucleic acids by recombinant DNA methods is well within the ability of one skilled in the art. Codon optimization, for purposes of maximizing recombinant protein yields in particular cell backgrounds, is also well within the ability of one skilled in the art. Administration of an isolated nucleic acid encoding the fusion protein is encompassed by the expression "administering a therapeutically effective amount of a fusion protein of the invention." Gene therapy methods are well known in the art. See, e.g., WO96/07321 which discloses the use of gene therapy methods to generate intracellular antibodies. Gene therapy methods have also been successfully demonstrated in human patients. See, e.g., Baumgartner et al., 1998, *Circulation* 97: 12, 1114-1123, and more recently, Fatham, 2007, "A gene therapy approach to treatment of autoimmune diseases," *Immun. Res.* 18:15-26; and U.S. Pat. No. 7,378,089, both incorporated herein by reference. See also Bainbridge et al., 2008, "Effect of gene therapy on visual function in Leber's congenital Amaurosis," *N Engl Med* 358:2231-2239; and Maguire et al., 2008, "Safety and efficacy of gene transfer for Leber's congenital Amaurosis," *N Engl J Med* 358:2240-8. There are two major approaches for introducing a nucleic acid encoding the fusion protein (optionally contained in a vector) into a patients cells: in vivo and ex vivo. For in vivo delivery, the nucleic acid is injected directly into the patient, usually at the site where the fusion protein is required. For ex vivo treatment, the patient's cells are removed, the nucleic acid is introduced into these isolated cells and the modified cells are administered to the patient either directly or, for example, encapsulated within porous membranes which are implanted into the patient (see, e.g., U.S. Pat. Nos. 4,892,538 and 5,283,187). There are a variety of techniques available for introducing nucleic acids into viable cells. The techniques vary depending upon whether the nucleic acid is transferred into cultured cells in vitro, or in vivo in the cells of the intended host. Techniques suitable for the transfer of nucleic acid into mammalian cells in vitro include the use of liposomes, electroporation, microinjection, cell fusion, DEAE-dextran, the calcium phosphate precipitation method, etc. Commonly used vectors for ex vivo delivery of the gene are retroviral and lentiviral vectors.

Preferred in vivo nucleic acid transfer techniques include transfection with viral vectors such as adenovirus, Herpes simplex I virus, adeno-associated virus), lipid-based systems (useful lipids for lipid-mediated transfer of the gene are DOTMA, DOPE and DC-Chol, for example), naked DNA, and transposon-based expression systems. For review of the currently known gene marking and gene therapy protocols see Anderson et al., *Science* 256:808-813 (1992). See also WO 93/25673 and the references cited therein.

"Gene therapy" includes both conventional gene therapy where a lasting effect is achieved by a single treatment, and the administration of gene therapeutic agents, which involves the one time or repeated administration of a therapeutically effective DNA or mRNA. Oligonucleotides can be modified to enhance their uptake, e.g. by substituting their negatively charged phosphodiester groups by uncharged groups. Fusion proteins of the present invention can be delivered using gene therapy methods, for example locally in tumor beds, intrathecally, or systemically (e.g., via vectors that selectively target specific tissue types, for example, tissue-specific adeno-associated viral vectors). In some embodiments, primary cells (such as lymphocytes or stem cells) from the individual can be transfected ex vivo with a gene encoding any of the fusion proteins of the present invention, and then returning the transfected cells to the individual's body.

"Treating" or "treatment" refers to therapeutic treatment, wherein the object is to prevent or slow down (lessen) the targeted pathologic condition or disorder. A subject is successfully "treated" if: after receiving a therapeutic amount of a fusion protein of the invention according to the methods of the present invention, the subject shows observable and/or measurable reduction in or absence of one or more signs and symptoms of the particular disease. For example, for cancer, reduction in the number of cancer cells or absence of the cancer cells; reduction in the tumor size; inhibition (i.e., slow to some extent and preferably stop) of tumor metastasis; inhibition, to some extent, of tumor growth; increase in length of remission, and/or relief to some extent, one or more of the symptoms associated with the specific cancer; reduced morbidity and mortality, and improvement in quality of life issues. Reduction of the signs or symptoms of a disease may also be felt by the patient. Treatment can achieve a complete response, defined as disappearance of all signs of cancer, or a partial response, wherein the size of the tumor is decreased, preferably by more than 50%, more preferably by 75%. A patient is also considered treated if the patient experiences a stabilization of disease. These parameters for assessing successful treatment and improvement in the disease are readily measurable by routine procedures familiar to a physician of appropriate skill in the art.

In the context of treatment for cancer, the fusion proteins of the present invention can optionally be administered to a patient in combination with other chemotherapeutic agents. Suitable chemotherapeutic agents include, for example, alkylating agents such as thiotepa and cyclosphosphamide (CYTOXAN™); alkyl sulfonates such as busulfan, improsiilfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; nitrogen mustards such as chlorambucil, chlomaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, caminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK.R™; razoxane; sizofiran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxanes, e.g. paclitaxel (TAXOL.R™, Bristol-Myers Squibb Oncology, Princeton, N.J.) and docetaxel (TAXOTERE.R™, Rhone-Poulenc Rorer, Antony, France); chlorambucil; gemcitabine; 6-thioguanine; mercaptopurine;

methotrexate; platinum analogs such as cisplatin and carboplatin; vinblastine; platinum; etoposide (VP-16); Ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RFS 2000; difluoromethylomithine (DMFO); retinoic acid; esperamicins; capecitabine; and pharmaceutically acceptable salts, acids or derivatives of any of the above.

Other chemotherapeutic agents further include anti-hormonal agents that act to regulate or inhibit hormone action on tumors such as anti-estrogens including for example tamoxifen, raloxifene, aromatase inhibiting 4(5)-imidazoles, 4-hydroxytamoxifen, trioxifene, keoxifene, LY117018, onapristone, and toremifene (Fareston); and anti-androgens such as flutamide, nilutamide, bicalutamide, leuprolide, and goserelin; and pharmaceutically acceptable salts, acids or derivatives of any of the above.

Other chemotherapeutic agents further chemotherapeutic agents that are able to sensitize tumour cells to TRAIL and overcome TRAIL resistance, such as proteasome inhibitors and histone deacetylase (HDAC) inhibitors, cycloheximide, imatinib mesylate and other protein tyrosine kinase inhibitors, 17-allylamino-17-demethoxygeldanamycin, arsenic trioxide and X-linked Inhibitors of Apoptosis Protein small molecule antagonists; and pharmaceutically acceptable salts, acids or derivatives of any of these.

Additional information on the methods of cancer treatment is provided in U.S. Pat. No. 7,285,522, incorporated by reference in its entirety The practice of the invention is illustrated by the following non-limiting example. The invention should not be construed to be limited solely to the compositions and methods described herein, but should be construed to include other compositions and methods as well. One of skill in the art will know that other compositions and methods are available to perform the procedures described herein.

The example below is described with respect to a representative fusion protein of the invention comprising a functional fragment of human SIRP alpha fused by way of a linker to a functional fragment of TRAIL. However, a person of skill in the art would understand how to conduct the corresponding experiments with any other embodiment of the fusion protein of the invention.

EXAMPLES

Example 1

A novel fusion protein comprising a soluble fragment of human SIRP alpha (Component A) fused to a functional fragment of the ectodomain of TRAIL (Component B) via an intervening peptide linker is prepared by sub-cloning PCR-amplified components into pMFneo expression vector.

The soluble fragment of human SIRP alpha in the fusion protein was SEQ ID NO: 1.

The ectodomain of TRAIL in the fusion protein was SEQ ID NO: 9.

The linker in the fusion protein was SEQ ID NO: 17. The fusion protein further comprised a purification tag at the N-terminal, having the sequence SEQ ID NO: 21.

The sequence of the fusion protein was SEQ ID NO: 14.
Production of Functional SIRP Alpha-TRAIL Protein Recombinant SIRP alpha-TRAIL is produced using a pMFneo eukaryotic expression system. The pMFneo-based expression construct is transiently transfected into HEK293 cells, and expression and secretion of the fusion protein is demonstrated by Western blot analysis of conditioned media.

A high-yield, multi-step chromatographic purification may be used for the isolation of highly-purified SIRP alpha-TRAIL protein. The process includes an efficient capture step based on the 6-His tag, an anion-exchange chromatography step, and then a final buffer exchange step, the latter carrying the product into the formulation buffer.

A seven-liter production fermentation followed by the above purification process, yields purified SIRP ALPHA-TRAIL, which may be used for in-vitro and in-vivo experiments, such as those indicated below.

To validate the identity of expressed SIRP alpha-TRAIL, its ability to bind to, and block binding of, CD47 to SIRP alpha-expressing macrophages, is assessed. An exemplary assay is to incubate CD47-expressing cells with macrophages, in the presence or absence of SIRP alpha-TRAIL and to assess the extent of phagocytosis and/or assay levels of tyrosine phosphorylation. For assay details, see, e.g., Jaiswal et al., (U.S. Pat. Appln. Pub. 2011/0014119).

The functionality of the TRAIL component of SIRP alpha-TRAIL is determined by evaluating its capacity to induce apoptosis in Jurkat T cells, measuring Annexin-V/PI staining by flow cytometry. Recombinant TRAIL (Super Killer TRAIL™) is used as a positive control in this experiment.

Assay for SIRP alpha-TRAIL-Driven Cytotoxicity Against Cancer Cells

Tumor cell cytotoxicity mediated by purified untagged human SIRP alpha-TRAIL protein is studied with several human tumor cell types. Human leukemia cell lines (e.g., HL-60), or tumor cell lines (e.g., HeLa cells), that express high levels of CD47 and TRAIL-R, are incubated with increasing concentrations of purified SIRP alpha-TRAIL, and the EC50 is measured.

Assessment of SIRP Alpha-TRAIL's Tumoricidal Activity Vs. Its Component Parts in Combination The tumoricidal effect of the SIRP alpha-TRAIL fusion protein is compared to the effect of its component parts added in combination. To this end, cell viability of theHL-60 or HeLa cells in the presence of phagocytotic cells, such as macrophages, is measured following incubation with either purified SIRP alpha-TRAIL, soluble extracellular domain of TRAIL (sTRAIL) alone, soluble SIRP alpha fused to the Fc domain of IgG1 (SIRP alpha-Fc), or the combination of both (SIRP alpha-Fc+sTRAIL), at similar molar concentrations.

This way, it may be demonstrated that SIRP alpha-TRAIL has substantial therapeutic benefit in facilitating cancer cell death, and this effect cannot be replicated by simply administering this fusion protein's two component elements as soluble agents in combination.

Apoptosis Assay

HL-60 cells are incubated with increasing concentrations of purified SIRP alpha-TRAIL, SIRP alpha-Fc, sTRAIL, or a combination of both (SIRP alpha-Fc+sTRAIL). Following incubation with the respective proteins, the treated cells are analyzed by FACS to determine the percentage of cells undergoing apoptosis, as assessed by annexin V/PI staining.

Phagocytosis Assay

HL-60 cells are incubated with macrophages and with increasing concentrations of purified SIRP alpha-TRAIL, SIRP alpha-Fc, sTRAIL, or a combination of both (SIRP alpha-Fc+sTRAIL). Following incubation with the respective proteins, the treated cells are analyzed for phagocytosis by either immunofluorescence microscopy or flow cytometry. For assay details, see, e.g., Jaiswal et al., (U.S. Pat. Appln. Pub. 2011/0014119).

Whereas particular embodiments of this invention have been described above for purposes of illustration, it will be evident to those skilled in the art that numerous variations of the details of the present invention may be made without departing from the invention as defined in the appended claims.

The disclosures of each and every patent, patent application, publication, GenBank UniProtKB, or SwissProt record cited herein are hereby incorporated herein by reference in their entirety.

One skilled in the art will readily appreciate that the present invention is well adapted to carry out the objects and obtain the ends and advantages mentioned, as well as those inherent therein. While the invention has been disclosed with reference to specific embodiments, it is apparent that other embodiments and variations of this invention may be devised by others skilled in the art without departing from the true spirit and scope used in the practice of the invention. The appended claims are intended to be construed to include all such embodiments and equivalent variations.

What is claimed is:

1. A fusion protein comprising Component A and Component B, wherein Component A comprises at least a portion of the ectodomain of SIRP alpha, and Component B comprises at least a portion of human TRAIL, and wherein the fusion protein further comprises a linker polypeptide between Components A and B, and wherein the fusion protein comprises the amino acid sequence of SEQ ID NO: 13.

2. A pharmaceutical composition comprising a pharmaceutically acceptable carrier and the fusion protein of claim 1.

3. A method of treating a proliferative disorder that is associated with CD47 expression in a patient comprising administering a therapeutically effective amount of the fusion protein of claim 1 to a patient in need of such treatment.

4. The method of claim 3, wherein the proliferative disorder is cancer.

5. The method of claim 4, wherein the cancer is a solid tumor.

6. The method of claim 4, wherein the cancer is pancreatic cancer, breast cancer, ovarian cancer, bladder cancer, melanoma, glioblastoma, acute lymphoblastic leukemia (ALL) or acute myelogenous leukemia (AML).

7. A pharmaceutical composition comprising a pharmaceutically acceptable carrier and the fusion protein of claim 1, for treatment of cancer, wherein the cancer cell expresses CD47 and/or TRAIL-R.

8. The pharmaceutical composition of claim 7, wherein the cancer is a solid tumor.

9. The pharmaceutical composition of claim 7, wherein the cancer is pancreatic cancer, breast cancer, ovarian cancer, bladder cancer, melanoma, glioblastoma, acute lymphoblastic leukemia (ALL) or acute myelogenous leukemia (AML).

* * * * *

SEQUENCE LISTING

```
<160> NUMBER OF SEQ ID NOS: 24

<210> SEQ ID NO 1
<211> LENGTH: 347
<212> TYPE: PRT
<213> ORGANISM: Homo sapiens

<400> SEQUENCE: 1

Gly Val Ala Gly Glu Glu Glu Leu Gln Val Ile Gln Pro Asp Lys Ser
1               5                   10                  15

Val Leu Val Ala Ala Gly Glu Thr Ala Thr Leu Arg Cys Thr Ala Thr
                20                  25                  30

Ser Leu Ile Pro Val Gly Pro Ile Gln Trp Phe Arg Gly Ala Gly Pro
            35                  40                  45

Gly Arg Glu Leu Ile Tyr Asn Gln Lys Glu Gly His Phe Pro Arg Val
        50                  55                  60

Thr Thr Val Ser Asp Leu Thr Lys Arg Asn Asn Met Asp Phe Ser Ile
65                  70                  75                  80

Arg Ile Gly Asn Ile Thr Pro Ala Asp Ala Gly Thr Tyr Tyr Cys Val
                85                  90                  95

Lys Phe Arg Lys Gly Ser Pro Asp Asp Val Glu Phe Lys Ser Gly Ala
            100                 105                 110

Gly Thr Glu Leu Ser Val Arg Ala Lys Pro Ser Ala Pro Val Val Ser
        115                 120                 125

Gly Pro Ala Ala Arg Ala Thr Pro Gln His Thr Val Ser Phe Thr Cys
    130                 135                 140

Glu Ser His Gly Phe Ser Pro Arg Asp Ile Thr Leu Lys Trp Phe Lys
145                 150                 155                 160

Asn Gly Asn Glu Leu Ser Asp Phe Gln Thr Asn Val Asp Pro Val Gly
                165                 170                 175

Glu Ser Val Ser Tyr Ser Ile His Ser Thr Ala Lys Val Val Leu Thr
            180                 185                 190

Arg Glu Asp Val His Ser Gln Val Ile Cys Glu Val Ala His Val Thr
        195                 200                 205

Leu Gln Gly Asp Pro Leu Arg Gly Thr Ala Asn Leu Ser Glu Thr Ile
    210                 215                 220

Arg Val Pro Pro Thr Leu Glu Val Thr Gln Gln Pro Val Arg Ala Glu
225                 230                 235                 240

Asn Gln Val Asn Val Thr Cys Gln Val Arg Lys Phe Tyr Pro Gln Arg
                245                 250                 255

Leu Gln Leu Thr Trp Leu Glu Asn Gly Asn Val Ser Arg Thr Glu Thr
            260                 265                 270
```

```
Ala Ser Thr Val Thr Glu Asn Lys Asp Gly Thr Tyr Asn Trp Met Ser
            275                 280                 285

Trp Leu Leu Val Asn Val Ser Ala His Arg Asp Asp Val Lys Leu Thr
    290                 295                 300

Cys Gln Val Glu His Asp Gly Gln Pro Ala Val Ser Lys Ser His Asp
305                 310                 315                 320

Leu Lys Val Ser Ala His Pro Lys Glu Gln Gly Ser Asn Thr Ala Ala
            325                 330                 335

Glu Asn Thr Gly Ser Asn Glu Arg Asn Ile Tyr
            340                 345

<210> SEQ ID NO 2
<211> LENGTH: 341
<212> TYPE: PRT
<213> ORGANISM: Homo sapiens

<400> SEQUENCE: 2

Gly Glu Glu Glu Leu Gln Val Ile Gln Pro Asp Lys Ser Val Leu Val
1               5                  10                  15

Ala Ala Gly Glu Thr Ala Thr Leu Arg Cys Thr Ala Thr Ser Leu Ile
            20                  25                  30

Pro Val Gly Pro Ile Gln Trp Phe Arg Gly Ala Gly Pro Gly Arg Glu
        35                  40                  45

Leu Ile Tyr Asn Gln Lys Glu Gly His Phe Pro Arg Val Thr Thr Val
    50                  55                  60

Ser Asp Leu Thr Lys Arg Asn Asn Met Asp Phe Ser Ile Arg Ile Gly
65                  70                  75                  80

Asn Ile Thr Pro Ala Asp Ala Gly Thr Tyr Tyr Cys Val Lys Phe Arg
                85                  90                  95

Lys Gly Ser Pro Asp Asp Val Glu Phe Lys Ser Gly Ala Gly Thr Glu
            100                 105                 110

Leu Ser Val Arg Ala Lys Pro Ser Ala Pro Val Val Ser Gly Pro Ala
        115                 120                 125

Ala Arg Ala Thr Pro Gln His Thr Val Ser Phe Thr Cys Glu Ser His
130                 135                 140

Gly Phe Ser Pro Arg Asp Ile Thr Leu Lys Trp Phe Lys Asn Gly Asn
145                 150                 155                 160

Glu Leu Ser Asp Phe Gln Thr Asn Val Asp Pro Val Gly Glu Ser Val
                165                 170                 175

Ser Tyr Ser Ile His Ser Thr Ala Lys Val Val Leu Thr Arg Glu Asp
            180                 185                 190

Val His Ser Gln Val Ile Cys Glu Val Ala His Val Thr Leu Gln Gly
        195                 200                 205

Asp Pro Leu Arg Gly Thr Ala Asn Leu Ser Glu Thr Ile Arg Val Pro
    210                 215                 220

Pro Thr Leu Glu Val Thr Gln Gln Pro Val Arg Ala Glu Asn Gln Val
225                 230                 235                 240

Asn Val Thr Cys Gln Val Arg Lys Phe Tyr Pro Gln Arg Leu Gln Leu
                245                 250                 255

Thr Trp Leu Glu Asn Gly Asn Val Ser Arg Thr Glu Thr Ala Ser Thr
            260                 265                 270

Val Thr Glu Asn Lys Asp Gly Thr Tyr Asn Trp Met Ser Trp Leu Leu
        275                 280                 285

Val Asn Val Ser Ala His Arg Asp Asp Val Lys Leu Thr Cys Gln Val
```

```
                    290                 295                 300

Glu His Asp Gly Gln Pro Ala Val Ser Lys Ser His Asp Leu Lys Val
305                 310                 315                 320

Ser Ala His Pro Lys Glu Gln Gly Ser Asn Thr Ala Ala Glu Asn Thr
                    325                 330                 335

Gly Ser Asn Glu Arg
            340

<210> SEQ ID NO 3
<211> LENGTH: 332
<212> TYPE: PRT
<213> ORGANISM: Homo sapiens

<400> SEQUENCE: 3

Val Ala Gly Glu Glu Leu Gln Met Ile Gln Pro Glu Lys Leu Leu
1               5                   10                  15

Leu Val Thr Val Gly Lys Thr Ala Thr Leu His Cys Thr Val Thr Ser
                20                  25                  30

Leu Leu Pro Val Gly Pro Val Leu Trp Phe Arg Gly Val Gly Pro Gly
                35                  40                  45

Arg Glu Leu Ile Tyr Asn Gln Lys Glu Gly His Phe Pro Arg Val Thr
50                  55                  60

Thr Val Ser Asp Leu Thr Lys Arg Asn Asn Met Asp Phe Ser Ile Arg
65                  70                  75                  80

Ile Ser Ser Ile Thr Pro Ala Asp Val Gly Thr Tyr Tyr Cys Val Lys
                85                  90                  95

Phe Arg Lys Gly Ser Pro Glu Asn Val Glu Phe Lys Ser Gly Pro Gly
                100                 105                 110

Thr Glu Met Ala Leu Gly Ala Lys Pro Ser Ala Pro Val Val Leu Gly
                115                 120                 125

Pro Ala Ala Arg Thr Thr Pro Glu His Thr Val Ser Phe Thr Cys Glu
130                 135                 140

Ser His Gly Phe Ser Pro Arg Asp Ile Thr Leu Lys Trp Phe Lys Asn
145                 150                 155                 160

Gly Asn Glu Leu Ser Asp Phe Gln Thr Asn Val Asp Pro Thr Gly Gln
                165                 170                 175

Ser Val Ala Tyr Ser Ile Arg Ser Thr Ala Arg Val Val Leu Asp Pro
                180                 185                 190

Trp Asp Val Arg Ser Gln Val Ile Cys Glu Val Ala His Val Thr Leu
            195                 200                 205

Gln Gly Asp Pro Leu Arg Gly Thr Ala Asn Leu Ser Glu Ala Ile Arg
210                 215                 220

Val Pro Pro Thr Leu Glu Val Thr Gln Gln Pro Met Arg Val Gly Asn
225                 230                 235                 240

Gln Val Asn Val Thr Cys Gln Val Arg Lys Phe Tyr Pro Gln Ser Leu
                245                 250                 255

Gln Leu Thr Trp Ser Glu Asn Gly Asn Val Cys Gln Arg Glu Thr Ala
                260                 265                 270

Ser Thr Leu Thr Glu Asn Lys Asp Gly Thr Tyr Asn Trp Thr Ser Trp
                275                 280                 285

Phe Leu Val Asn Ile Ser Asp Gln Arg Asp Val Val Leu Thr Cys
                290                 295                 300

Gln Val Lys His Asp Gly Gln Leu Ala Val Ser Lys Arg Leu Ala Leu
305                 310                 315                 320
```

```
Glu Val Thr Val His Gln Lys Asp Gln Ser Ser Asp
                325                 330
```

```
<210> SEQ ID NO 4
<211> LENGTH: 133
<212> TYPE: PRT
<213> ORGANISM: Homo sapiens

<400> SEQUENCE: 4

Leu Gly Ser Ala Cys Cys Gly Ser Ala Gln Leu Leu Phe Asn Lys Thr
1               5                   10                  15

Lys Ser Val Glu Phe Thr Phe Cys Asn Asp Thr Val Val Ile Pro Cys
            20                  25                  30

Phe Val Thr Asn Met Glu Ala Gln Asn Thr Thr Glu Val Tyr Val Lys
        35                  40                  45

Trp Lys Phe Lys Gly Arg Asp Ile Tyr Thr Phe Asp Gly Ala Leu Asn
    50                  55                  60

Lys Ser Thr Val Pro Thr Asp Phe Ser Ser Ala Lys Ile Glu Val Ser
65                  70                  75                  80

Gln Leu Leu Lys Gly Asp Ala Ser Leu Lys Met Asp Lys Ser Asp Ala
                85                  90                  95

Val Ser His Thr Gly Asn Tyr Thr Cys Glu Val Thr Glu Leu Thr Arg
            100                 105                 110

Glu Gly Glu Thr Ile Ile Glu Leu Lys Tyr Arg Val Val Ser Trp Phe
        115                 120                 125

Ser Pro Asn Glu Asn
    130
```

```
<210> SEQ ID NO 5
<211> LENGTH: 124
<212> TYPE: PRT
<213> ORGANISM: Homo sapiens

<400> SEQUENCE: 5

Gln Leu Leu Phe Asn Lys Thr Lys Ser Val Glu Phe Thr Phe Cys Asn
1               5                   10                  15

Asp Thr Val Val Ile Pro Cys Phe Val Thr Asn Met Glu Ala Gln Asn
            20                  25                  30

Thr Thr Glu Val Tyr Val Lys Trp Lys Phe Lys Gly Arg Asp Ile Tyr
        35                  40                  45

Thr Phe Asp Gly Ala Leu Asn Lys Ser Thr Val Pro Thr Asp Phe Ser
    50                  55                  60

Ser Ala Lys Ile Glu Val Ser Gln Leu Leu Lys Gly Asp Ala Ser Leu
65                  70                  75                  80

Lys Met Asp Lys Ser Asp Ala Val Ser His Thr Gly Asn Tyr Thr Cys
                85                  90                  95

Glu Val Thr Glu Leu Thr Arg Glu Gly Glu Thr Ile Ile Glu Leu Lys
            100                 105                 110

Tyr Arg Val Val Ser Trp Phe Ser Pro Asn Glu Asn
        115                 120
```

```
<210> SEQ ID NO 6
<211> LENGTH: 281
<212> TYPE: PRT
<213> ORGANISM: Homo sapiens

<400> SEQUENCE: 6

Met Ala Met Met Glu Val Gln Gly Gly Pro Ser Leu Gly Gln Thr Cys
```

```
               1               5                    10                   15
             Val Leu Ile Val Ile Phe Thr Val Leu Leu Gln Ser Leu Cys Val Ala
                             20                   25                   30

Val Thr Tyr Val Tyr Phe Thr Asn Glu Leu Lys Gln Met Gln Asp Lys
                             35                   40                   45

Tyr Ser Lys Ser Gly Ile Ala Cys Phe Leu Lys Glu Asp Asp Ser Tyr
                             50                   55                   60

Trp Asp Pro Asn Asp Glu Glu Ser Met Asn Ser Pro Cys Trp Gln Val
             65                           70                   75                   80

Lys Trp Gln Leu Arg Gln Leu Val Arg Lys Met Ile Leu Arg Thr Ser
                             85                   90                   95

Glu Glu Thr Ile Ser Thr Val Gln Glu Lys Gln Gln Asn Ile Ser Pro
                            100                  105                  110

Leu Val Arg Glu Arg Gly Pro Gln Arg Val Ala Ala His Ile Thr Gly
                            115                  120                  125

Thr Arg Gly Arg Ser Asn Thr Leu Ser Ser Pro Asn Ser Lys Asn Glu
                            130                  135                  140

Lys Ala Leu Gly Arg Lys Ile Asn Ser Trp Glu Ser Ser Arg Ser Gly
             145                          150                  155                  160

His Ser Phe Leu Ser Asn Leu His Leu Arg Asn Gly Glu Leu Val Ile
                            165                  170                  175

His Glu Lys Gly Phe Tyr Tyr Ile Tyr Ser Gln Thr Tyr Phe Arg Phe
                            180                  185                  190

Gln Glu Glu Ile Lys Glu Asn Thr Lys Asn Asp Lys Gln Met Val Gln
                            195                  200                  205

Tyr Ile Tyr Lys Tyr Thr Ser Tyr Pro Asp Pro Ile Leu Leu Met Lys
                            210                  215                  220

Ser Ala Arg Asn Ser Cys Trp Ser Lys Asp Ala Glu Tyr Gly Leu Tyr
             225                          230                  235                  240

Ser Ile Tyr Gln Gly Gly Ile Phe Glu Leu Lys Glu Asn Asp Arg Ile
                            245                  250                  255

Phe Val Ser Val Thr Asn Glu His Leu Ile Asp Met Asp His Glu Ala
                            260                  265                  270

Ser Phe Phe Gly Ala Phe Leu Val Gly
                            275                  280

<210> SEQ ID NO 7
<211> LENGTH: 184
<212> TYPE: PRT
<213> ORGANISM: Homo sapiens

<400> SEQUENCE: 7

Glu Thr Ile Ser Thr Val Gln Glu Lys Gln Gln Asn Ile Ser Pro Leu
             1               5                    10                   15

Val Arg Glu Arg Gly Pro Gln Arg Val Ala Ala His Ile Thr Gly Thr
                             20                   25                   30

Arg Gly Arg Ser Asn Thr Leu Ser Ser Pro Asn Ser Lys Asn Glu Lys
                             35                   40                   45

Ala Leu Gly Arg Lys Ile Asn Ser Trp Glu Ser Ser Arg Ser Gly His
                             50                   55                   60

Ser Phe Leu Ser Asn Leu His Leu Arg Asn Gly Glu Leu Val Ile His
             65                           70                   75                   80

Glu Lys Gly Phe Tyr Tyr Ile Tyr Ser Gln Thr Tyr Phe Arg Phe Gln
                             85                   90                   95
```

Glu Glu Ile Lys Glu Asn Thr Lys Asn Asp Lys Gln Met Val Gln Tyr
            100                 105                 110

Ile Tyr Lys Tyr Thr Ser Tyr Pro Asp Pro Ile Leu Leu Met Lys Ser
        115                 120                 125

Ala Arg Asn Ser Cys Trp Ser Lys Asp Ala Glu Tyr Gly Leu Tyr Ser
    130                 135                 140

Ile Tyr Gln Gly Gly Ile Phe Glu Leu Lys Glu Asn Asp Arg Ile Phe
145                 150                 155                 160

Val Ser Val Thr Asn Glu His Leu Ile Asp Met Asp His Glu Ala Ser
                165                 170                 175

Phe Phe Gly Ala Phe Leu Val Gly
            180

<210> SEQ ID NO 8
<211> LENGTH: 165
<212> TYPE: PRT
<213> ORGANISM: Homo sapiens

<400> SEQUENCE: 8

Arg Gly Pro Gln Arg Val Ala Ala His Ile Thr Gly Thr Arg Gly Arg
1               5                   10                  15

Ser Asn Thr Leu Ser Ser Pro Asn Ser Lys Asn Glu Lys Ala Leu Gly
            20                  25                  30

Arg Lys Ile Asn Ser Trp Glu Ser Ser Arg Ser Gly His Ser Phe Leu
        35                  40                  45

Ser Asn Leu His Leu Arg Asn Gly Glu Leu Val Ile His Glu Lys Gly
    50                  55                  60

Phe Tyr Tyr Ile Tyr Ser Gln Thr Tyr Phe Arg Phe Gln Glu Glu Ile
65                  70                  75                  80

Lys Glu Asn Thr Lys Asn Asp Lys Gln Met Val Gln Tyr Ile Tyr Lys
                85                  90                  95

Tyr Thr Ser Tyr Pro Asp Pro Ile Leu Leu Met Lys Ser Ala Arg Asn
            100                 105                 110

Ser Cys Trp Ser Lys Asp Ala Glu Tyr Gly Leu Tyr Ser Ile Tyr Gln
        115                 120                 125

Gly Gly Ile Phe Glu Leu Lys Glu Asn Asp Arg Ile Phe Val Ser Val
    130                 135                 140

Thr Asn Glu His Leu Ile Asp Met Asp His Glu Ala Ser Phe Phe Gly
145                 150                 155                 160

Ala Phe Leu Val Gly
            165

<210> SEQ ID NO 9
<211> LENGTH: 168
<212> TYPE: PRT
<213> ORGANISM: Homo sapiens

<400> SEQUENCE: 9

Val Arg Glu Arg Gly Pro Gln Arg Val Ala Ala His Ile Thr Gly Thr
1               5                   10                  15

Arg Gly Arg Ser Asn Thr Leu Ser Ser Pro Asn Ser Lys Asn Glu Lys
            20                  25                  30

Ala Leu Gly Arg Lys Ile Asn Ser Trp Glu Ser Ser Arg Ser Gly His
        35                  40                  45

Ser Phe Leu Ser Asn Leu His Leu Arg Asn Gly Glu Leu Val Ile His
    50                  55                  60

```
Glu Lys Gly Phe Tyr Tyr Ile Tyr Ser Gln Thr Tyr Phe Arg Phe Gln
 65                  70                  75                  80

Glu Glu Ile Lys Glu Asn Thr Lys Asn Asp Lys Gln Met Val Gln Tyr
                 85                  90                  95

Ile Tyr Lys Tyr Thr Ser Tyr Pro Asp Pro Ile Leu Leu Met Lys Ser
            100                 105                 110

Ala Arg Asn Ser Cys Trp Ser Lys Asp Ala Glu Tyr Gly Leu Tyr Ser
        115                 120                 125

Ile Tyr Gln Gly Gly Ile Phe Glu Leu Lys Glu Asn Asp Arg Ile Phe
    130                 135                 140

Val Ser Val Thr Asn Glu His Leu Ile Asp Met Asp His Glu Ala Ser
145                 150                 155                 160

Phe Phe Gly Ala Phe Leu Val Gly
                165

<210> SEQ ID NO 10
<211> LENGTH: 287
<212> TYPE: PRT
<213> ORGANISM: Homo sapiens

<400> SEQUENCE: 10

Met Gln Gln Pro Phe Asn Tyr Pro Tyr Pro Gln Ile Tyr Trp Val Asp
 1               5                  10                  15

Ser Ser Ala Ser Ser Pro Trp Ala Pro Pro Gly Thr Val Leu Pro Cys
             20                  25                  30

Pro Thr Ser Val Pro Arg Arg Pro Gly Gln Arg Arg Pro Pro Pro Pro
         35                  40                  45

Pro Pro Pro Pro Pro Leu Pro Pro Pro Pro Pro Pro Pro Pro Leu Pro
 50                  55                  60

Pro Leu Pro Leu Pro Pro Leu Lys Lys Arg Gly Asn His Ser Thr Gly
 65                  70                  75                  80

Leu Cys Leu Leu Val Met Phe Phe Met Val Leu Val Ala Leu Val Gly
                 85                  90                  95

Leu Gly Leu Gly Met Phe Gln Leu Phe His Leu Gln Lys Glu Leu Ala
            100                 105                 110

Glu Leu Arg Glu Ser Thr Ser Gln Met His Thr Ala Ser Ser Leu Glu
        115                 120                 125

Lys Gln Ile Gly His Pro Ser Pro Pro Pro Glu Lys Lys Glu Leu Arg
    130                 135                 140

Lys Val Ala His Leu Thr Gly Lys Ser Asn Ser Arg Ser Met Pro Leu
145                 150                 155                 160

Glu Trp Glu Asp Thr Tyr Gly Ile Val Leu Leu Ser Gly Val Lys Tyr
                165                 170                 175

Lys Lys Gly Gly Leu Val Ile Asn Glu Thr Gly Leu Tyr Phe Val Tyr
            180                 185                 190

Ser Lys Val Tyr Phe Arg Gly Gln Ser Cys Asn Asn Leu Pro Leu Ser
        195                 200                 205

His Lys Val Tyr Met Arg Asn Ser Lys Tyr Pro Gln Asp Leu Val Met
    210                 215                 220

Met Glu Gly Lys Met Met Ser Tyr Cys Thr Thr Gly Gln Met Trp Ala
225                 230                 235                 240

Arg Ser Ser Tyr Leu Gly Ala Val Phe Asn Leu Thr Ser Ala Asp His
                245                 250                 255

Leu Tyr Val Asn Val Ser Glu Leu Ser Leu Val Asn Phe Glu Glu Ser
            260                 265                 270
```

Gln Thr Phe Phe Gly Leu Tyr Lys Leu Ser Glu Gln Ile Asp Asn
        275                 280                 285

<210> SEQ ID NO 11
<211> LENGTH: 155
<212> TYPE: PRT
<213> ORGANISM: Homo sapiens

<400> SEQUENCE: 11

Leu Glu Lys Gln Ile Gly His Pro Ser Pro Pro Glu Lys Lys Glu
1               5                   10                  15

Leu Arg Lys Val Ala His Leu Thr Gly Lys Ser Asn Ser Arg Ser Met
                20                  25                  30

Pro Leu Glu Trp Glu Asp Thr Tyr Gly Ile Val Leu Leu Ser Gly Val
            35                  40                  45

Lys Tyr Lys Lys Gly Gly Leu Val Ile Asn Glu Thr Gly Leu Tyr Phe
    50                  55                  60

Val Tyr Ser Lys Val Tyr Phe Arg Gly Gln Ser Cys Asn Asn Leu Pro
65                  70                  75                  80

Leu Ser His Lys Val Tyr Met Arg Asn Ser Lys Tyr Pro Gln Asp Leu
                85                  90                  95

Val Met Met Glu Gly Lys Met Met Ser Tyr Cys Thr Thr Gly Gln Met
            100                 105                 110

Trp Ala Arg Ser Ser Tyr Leu Gly Ala Val Phe Asn Leu Thr Ser Ala
        115                 120                 125

Asp His Leu Tyr Val Asn Val Ser Glu Leu Ser Leu Val Asn Phe Glu
    130                 135                 140

Glu Ser Gln Thr Phe Phe Gly Leu Tyr Lys Leu
145                 150                 155

<210> SEQ ID NO 12
<211> LENGTH: 154
<212> TYPE: PRT
<213> ORGANISM: Homo sapiens

<400> SEQUENCE: 12

Glu Lys Gln Ile Gly His Pro Ser Pro Pro Glu Lys Lys Glu Leu
1               5                   10                  15

Arg Lys Val Ala His Leu Thr Gly Lys Ser Asn Ser Arg Ser Met Pro
                20                  25                  30

Leu Glu Trp Glu Asp Thr Tyr Gly Ile Val Leu Leu Ser Gly Val Lys
            35                  40                  45

Tyr Lys Lys Gly Gly Leu Val Ile Asn Glu Thr Gly Leu Tyr Phe Val
    50                  55                  60

Tyr Ser Lys Val Tyr Phe Arg Gly Gln Ser Cys Asn Asn Leu Pro Leu
65                  70                  75                  80

Ser His Lys Val Tyr Met Arg Asn Ser Lys Tyr Pro Gln Asp Leu Val
                85                  90                  95

Met Met Glu Gly Lys Met Met Ser Tyr Cys Thr Thr Gly Gln Met Trp
            100                 105                 110

Ala Arg Ser Ser Tyr Leu Gly Ala Val Phe Asn Leu Thr Ser Ala Asp
        115                 120                 125

His Leu Tyr Val Asn Val Ser Glu Leu Ser Leu Val Asn Phe Glu Glu
    130                 135                 140

Ser Gln Thr Phe Phe Gly Leu Tyr Lys Leu
145                 150

<210> SEQ ID NO 13
<211> LENGTH: 552
<212> TYPE: PRT
<213> ORGANISM: Artificial Sequence
<220> FEATURE:
<223> OTHER INFORMATION: SIRP alpha/TRAIL fusion protein

<400> SEQUENCE: 13

```
Gly Val Ala Gly Glu Glu Leu Gln Val Ile Gln Pro Asp Lys Ser
1               5                   10                  15

Val Leu Val Ala Ala Gly Glu Thr Ala Thr Leu Arg Cys Thr Ala Thr
                20                  25                  30

Ser Leu Ile Pro Val Gly Pro Ile Gln Trp Phe Arg Gly Ala Gly Pro
            35                  40                  45

Gly Arg Glu Leu Ile Tyr Asn Gln Lys Glu Gly His Phe Pro Arg Val
        50                  55                  60

Thr Thr Val Ser Asp Leu Thr Lys Arg Asn Asn Met Asp Phe Ser Ile
65                  70                  75                  80

Arg Ile Gly Asn Ile Thr Pro Ala Asp Ala Gly Thr Tyr Tyr Cys Val
                85                  90                  95

Lys Phe Arg Lys Gly Ser Pro Asp Asp Val Glu Phe Lys Ser Gly Ala
                100                 105                 110

Gly Thr Glu Leu Ser Val Arg Ala Lys Pro Ser Ala Pro Val Val Ser
            115                 120                 125

Gly Pro Ala Ala Arg Ala Thr Pro Gln His Thr Val Ser Phe Thr Cys
        130                 135                 140

Glu Ser His Gly Phe Ser Pro Arg Asp Ile Thr Leu Lys Trp Phe Lys
145                 150                 155                 160

Asn Gly Asn Glu Leu Ser Asp Phe Gln Thr Asn Val Asp Pro Val Gly
                165                 170                 175

Glu Ser Val Ser Tyr Ser Ile His Ser Thr Ala Lys Val Val Leu Thr
            180                 185                 190

Arg Glu Asp Val His Ser Gln Val Ile Cys Glu Val Ala His Val Thr
        195                 200                 205

Leu Gln Gly Asp Pro Leu Arg Gly Thr Ala Asn Leu Ser Glu Thr Ile
    210                 215                 220

Arg Val Pro Pro Thr Leu Glu Val Thr Gln Gln Pro Val Arg Ala Glu
225                 230                 235                 240

Asn Gln Val Asn Val Thr Cys Gln Val Arg Lys Phe Tyr Pro Gln Arg
                245                 250                 255

Leu Gln Leu Thr Trp Leu Glu Asn Gly Asn Val Ser Arg Thr Glu Thr
            260                 265                 270

Ala Ser Thr Val Thr Glu Asn Lys Asp Gly Thr Tyr Asn Trp Met Ser
        275                 280                 285

Trp Leu Leu Val Asn Val Ser Ala His Arg Asp Asp Val Lys Leu Thr
    290                 295                 300

Cys Gln Val Glu His Asp Gly Gln Pro Ala Val Ser Lys Ser His Asp
305                 310                 315                 320

Leu Lys Val Ser Ala His Pro Lys Glu Gln Gly Ser Asn Thr Ala Ala
                325                 330                 335

Glu Asn Thr Gly Ser Asn Glu Arg Asn Ile Tyr Gly Asp Pro Leu Val
            340                 345                 350

Thr Ala Ala Ser Val Leu Glu Phe Gly Gly Ser Gly Gly Gly Ser Glu
        355                 360                 365
```

```
Gly Gly Gly Ser Glu Gly Gly Ser Glu Gly Gly Ser Asp Ile
        370             375             380

Val Arg Glu Arg Gly Pro Gln Arg Val Ala Ala His Ile Thr Gly Thr
385                 390                 395                 400

Arg Gly Arg Ser Asn Thr Leu Ser Ser Pro Asn Ser Lys Asn Glu Lys
                405                 410                 415

Ala Leu Gly Arg Lys Ile Asn Ser Trp Glu Ser Ser Arg Ser Gly His
                420                 425                 430

Ser Phe Leu Ser Asn Leu His Leu Arg Asn Gly Glu Leu Val Ile His
                435                 440                 445

Glu Lys Gly Phe Tyr Tyr Ile Tyr Ser Gln Thr Tyr Phe Arg Phe Gln
450                 455                 460

Glu Glu Ile Lys Glu Asn Thr Lys Asn Asp Lys Gln Met Val Gln Tyr
465                 470                 475                 480

Ile Tyr Lys Tyr Thr Ser Tyr Pro Asp Pro Ile Leu Leu Met Lys Ser
                485                 490                 495

Ala Arg Asn Ser Cys Trp Ser Lys Asp Ala Glu Tyr Gly Leu Tyr Ser
                500                 505                 510

Ile Tyr Gln Gly Gly Ile Phe Glu Leu Lys Glu Asn Asp Arg Ile Phe
                515                 520                 525

Val Ser Val Thr Asn Glu His Leu Ile Asp Met Asp His Glu Ala Ser
530                 535                 540

Phe Phe Gly Ala Phe Leu Val Gly
545                 550

<210> SEQ ID NO 14
<211> LENGTH: 561
<212> TYPE: PRT
<213> ORGANISM: Artificial Sequence
<220> FEATURE:
<223> OTHER INFORMATION: SIRP alpha/TRAIL fusion protein

<400> SEQUENCE: 14

Ala Ser His His His His His His Met Gly Val Ala Gly Glu Glu Glu
1               5                   10                  15

Leu Gln Val Ile Gln Pro Asp Lys Ser Val Leu Val Ala Ala Gly Glu
                20                  25                  30

Thr Ala Thr Leu Arg Cys Thr Ala Thr Ser Leu Ile Pro Val Gly Pro
            35                  40                  45

Ile Gln Trp Phe Arg Gly Ala Gly Pro Gly Arg Glu Leu Ile Tyr Asn
        50                  55                  60

Gln Lys Glu Gly His Phe Pro Arg Val Thr Thr Val Ser Asp Leu Thr
65                  70                  75                  80

Lys Arg Asn Asn Met Asp Phe Ser Ile Arg Ile Gly Asn Ile Thr Pro
                85                  90                  95

Ala Asp Ala Gly Thr Tyr Tyr Cys Val Lys Phe Arg Lys Gly Ser Pro
                100                 105                 110

Asp Asp Val Glu Phe Lys Ser Gly Ala Gly Thr Glu Leu Ser Val Arg
            115                 120                 125

Ala Lys Pro Ser Ala Pro Val Val Ser Gly Pro Ala Ala Arg Ala Thr
130                 135                 140

Pro Gln His Thr Val Ser Phe Thr Cys Glu Ser His Gly Phe Ser Pro
145                 150                 155                 160

Arg Asp Ile Thr Leu Lys Trp Phe Lys Asn Gly Asn Glu Leu Ser Asp
                165                 170                 175
```

Phe Gln Thr Asn Val Asp Pro Val Gly Glu Ser Val Ser Tyr Ser Ile
            180                 185                 190

His Ser Thr Ala Lys Val Val Leu Thr Arg Glu Asp Val His Ser Gln
        195                 200                 205

Val Ile Cys Glu Val Ala His Val Thr Leu Gln Gly Asp Pro Leu Arg
    210                 215                 220

Gly Thr Ala Asn Leu Ser Glu Thr Ile Arg Val Pro Pro Thr Leu Glu
225                 230                 235                 240

Val Thr Gln Gln Pro Val Arg Ala Glu Asn Gln Val Asn Val Thr Cys
                245                 250                 255

Gln Val Arg Lys Phe Tyr Pro Gln Arg Leu Gln Leu Thr Trp Leu Glu
            260                 265                 270

Asn Gly Asn Val Ser Arg Thr Glu Thr Ala Ser Thr Val Thr Glu Asn
        275                 280                 285

Lys Asp Gly Thr Tyr Asn Trp Met Ser Trp Leu Leu Val Asn Val Ser
    290                 295                 300

Ala His Arg Asp Asp Val Lys Leu Thr Cys Gln Val Glu His Asp Gly
305                 310                 315                 320

Gln Pro Ala Val Ser Lys Ser His Asp Leu Lys Val Ser Ala His Pro
                325                 330                 335

Lys Glu Gln Gly Ser Asn Thr Ala Ala Glu Asn Thr Gly Ser Asn Glu
            340                 345                 350

Arg Asn Ile Tyr Gly Asp Pro Leu Val Thr Ala Ala Ser Val Leu Glu
        355                 360                 365

Phe Gly Gly Ser Gly Gly Ser Glu Gly Gly Ser Glu Gly Gly
    370                 375                 380

Gly Ser Glu Gly Gly Gly Ser Asp Ile Val Arg Glu Arg Gly Pro Gln
385                 390                 395                 400

Arg Val Ala Ala His Ile Thr Gly Thr Arg Gly Arg Ser Asn Thr Leu
                405                 410                 415

Ser Ser Pro Asn Ser Lys Asn Glu Lys Ala Leu Gly Arg Lys Ile Asn
            420                 425                 430

Ser Trp Glu Ser Ser Arg Ser Gly His Ser Phe Leu Ser Asn Leu His
        435                 440                 445

Leu Arg Asn Gly Glu Leu Val Ile His Glu Lys Gly Phe Tyr Tyr Ile
    450                 455                 460

Tyr Ser Gln Thr Tyr Phe Arg Phe Gln Glu Glu Ile Lys Glu Asn Thr
465                 470                 475                 480

Lys Asn Asp Lys Gln Met Val Gln Tyr Ile Tyr Lys Tyr Thr Ser Tyr
                485                 490                 495

Pro Asp Pro Ile Leu Leu Met Lys Ser Ala Arg Asn Ser Cys Trp Ser
            500                 505                 510

Lys Asp Ala Glu Tyr Gly Leu Tyr Ser Ile Tyr Gln Gly Gly Ile Phe
        515                 520                 525

Glu Leu Lys Glu Asn Asp Arg Ile Phe Val Ser Val Thr Asn Glu His
    530                 535                 540

Leu Ile Asp Met Asp His Glu Ala Ser Phe Phe Gly Ala Phe Leu Val
545                 550                 555                 560

Gly

<210> SEQ ID NO 15
<211> LENGTH: 5
<212> TYPE: PRT

```
<213> ORGANISM: Artificial Sequence
<220> FEATURE:
<223> OTHER INFORMATION: linker

<400> SEQUENCE: 15

Gly Gly Gly Gly Ser
1               5

<210> SEQ ID NO 16
<211> LENGTH: 5
<212> TYPE: PRT
<213> ORGANISM: Artificial Sequence
<220> FEATURE:
<223> OTHER INFORMATION: linker

<400> SEQUENCE: 16

Gly Gly Gly Gly Ser
1               5

<210> SEQ ID NO 17
<211> LENGTH: 37
<212> TYPE: PRT
<213> ORGANISM: Artificial Sequence
<220> FEATURE:
<223> OTHER INFORMATION: linker

<400> SEQUENCE: 17

Gly Asp Pro Leu Val Thr Ala Ala Ser Val Leu Glu Phe Gly Gly Ser
1               5                   10                  15

Gly Gly Gly Ser Glu Gly Gly Ser Glu Gly Gly Ser Glu Gly
            20                  25                  30

Gly Gly Ser Asp Ile
        35

<210> SEQ ID NO 18
<211> LENGTH: 15
<212> TYPE: PRT
<213> ORGANISM: Artificial Sequence
<220> FEATURE:
<223> OTHER INFORMATION: hinge region of human IgG1 linker

<400> SEQUENCE: 18

Glu Pro Lys Ser Cys Asp Lys Thr His Thr Cys Pro Pro Cys Pro
1               5                   10                  15

<210> SEQ ID NO 19
<211> LENGTH: 247
<212> TYPE: PRT
<213> ORGANISM: Artificial Sequence
<220> FEATURE:
<223> OTHER INFORMATION: linker

<400> SEQUENCE: 19

Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80
```

```
Tyr Asn Ser Thr Tyr Arg Val Val Ser Val Leu Thr Val Leu His Gln
                 85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys Glu Pro Lys Ser Cys Asp Lys Thr
225                 230                 235                 240

His Thr Cys Pro Pro Cys Pro
                245

<210> SEQ ID NO 20
<211> LENGTH: 232
<212> TYPE: PRT
<213> ORGANISM: Artificial Sequence
<220> FEATURE:
<223> OTHER INFORMATION: linker

<400> SEQUENCE: 20

Glu Pro Lys Ser Ser Asp Lys Thr His Thr Ser Pro Pro Ser Pro Ala
1               5                   10                  15

Pro Pro Val Ala Gly Ala Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Ala Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190
```

Ser Lys Leu Thr Val Asp Lys Ser Arg Trp Gln Gln Gly Asn Val Phe
            195                 200                 205

Ser Cys Ser Val Met His Glu Ala Leu His Asn His Tyr Thr Gln Lys
        210                 215                 220

Ser Leu Ser Leu Ser Pro Gly Lys
225                 230

<210> SEQ ID NO 21
<211> LENGTH: 9
<212> TYPE: PRT
<213> ORGANISM: Artificial Sequence
<220> FEATURE:
<223> OTHER INFORMATION: purification tag

<400> SEQUENCE: 21

Ala Ser His His His His His His Met
1               5

<210> SEQ ID NO 22
<211> LENGTH: 54
<212> TYPE: PRT
<213> ORGANISM: Artificial Sequence
<220> FEATURE:
<223> OTHER INFORMATION: trimerization sequence

<400> SEQUENCE: 22

Gly Tyr Ile Pro Glu Ala Pro Arg Asp Gly Gln Ala Tyr Val Arg Lys
1               5                   10                  15

Arg Gly Glu Trp Val Leu Leu Ser Thr Phe Leu Gly Tyr Ile Pro Glu
            20                  25                  30

Ala Pro Arg Asp Gly Gln Ala Tyr Val Arg Lys Arg Gly Glu Trp Val
        35                  40                  45

Leu Leu Ser Thr Phe Leu
    50

<210> SEQ ID NO 23
<211> LENGTH: 24
<212> TYPE: PRT
<213> ORGANISM: Artificial Sequence
<220> FEATURE:
<223> OTHER INFORMATION: trimerization sequence

<400> SEQUENCE: 23

Val Thr Thr Leu Gln Asp Ser Ile Arg Lys Val Thr Glu Glu Asn Lys
1               5                   10                  15

Glu Leu Ala Asn Glu Leu Arg Arg
            20

<210> SEQ ID NO 24
<211> LENGTH: 8
<212> TYPE: PRT
<213> ORGANISM: Artificial Sequence
<220> FEATURE:
<223> OTHER INFORMATION: cell binding domain of thrombospondin-1

<400> SEQUENCE: 24

Arg Phe Tyr Val Val Met Trp Lys
1               5